United States Patent
Pemberton et al.

(10) Patent No.: US 10,114,028 B2
(45) Date of Patent: Oct. 30, 2018

(54) BIOMARKERS FOR PNEUMONIA AND ACUTE DECOMPENSATED HEART FAILURE

(71) Applicant: Otago Innovation Limited, Dunedin (NZ)

(72) Inventors: Christopher Joseph Pemberton, Christchurch (NZ); Arthur Mark Richards, Christchurch (NZ); Matthew Simon Byers, Christchurch (NZ)

(73) Assignee: Upstream Medical Technologies Limited, Christchurch (NZ)

( * ) Notice: Subject to any disclaimer, the term of this patent is extended or adjusted under 35 U.S.C. 154(b) by 0 days.

(21) Appl. No.: 13/844,449

(22) Filed: Mar. 15, 2013

(65) Prior Publication Data

US 2013/0296240 A1 Nov. 7, 2013

Related U.S. Application Data

(60) Provisional application No. 61/613,311, filed on Mar. 20, 2012.

(51) Int. Cl.

| G01N 33/74 | (2006.01) |
|---|---|
| C07K 16/26 | (2006.01) |
| C07K 14/575 | (2006.01) |
| C07K 14/63 | (2006.01) |
| G01N 33/68 | (2006.01) |

(52) U.S. Cl.
CPC .......... *G01N 33/74* (2013.01); *C07K 14/575* (2013.01); *C07K 14/63* (2013.01); *C07K 16/26* (2013.01); *G01N 33/6893* (2013.01); *G01N 2800/12* (2013.01); *G01N 2800/325* (2013.01)

(58) Field of Classification Search
None
See application file for complete search history.

(56) References Cited

U.S. PATENT DOCUMENTS

| 4,196,265 A | 4/1980 | Koprowski et al. |
|---|---|---|
| 4,816,567 A | 3/1989 | Cabilly et al. |
| 5,221,685 A | 6/1993 | Obata et al. |
| 5,310,687 A | 5/1994 | Bard et al. |
| 5,334,708 A | 8/1994 | Chang et al. |
| 5,480,792 A | 1/1996 | Buechler et al. |
| 5,504,013 A | 4/1996 | Senior |
| 5,525,524 A | 6/1996 | Buechler et al. |
| 5,571,698 A | 11/1996 | Ladner et al. |
| 5,631,171 A | 5/1997 | Sandstrom et al. |
| 5,647,124 A | 7/1997 | Chan et al. |
| 5,679,526 A | 10/1997 | Buechler et al. |
| 5,719,060 A | 2/1998 | Hutchens et al. |
| 5,719,600 A | 2/1998 | Alcorn |
| 5,744,305 A | 4/1998 | Fodor et al. |
| 5,792,294 A | 8/1998 | Randazzo et al. |
| 5,821,047 A | 10/1998 | Garrard et al. |
| 5,824,799 A | 10/1998 | Buechler et al. |
| 5,843,708 A | 12/1998 | Hardman et al. |
| 5,851,776 A | 12/1998 | Valkirs |
| 5,885,527 A | 5/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,020,153 A | 2/2000 | Hardman et al. |
| 6,057,098 A | 5/2000 | Buechler et al. |
| 6,107,623 A | 8/2000 | Bateman et al. |
| 6,113,855 A | 9/2000 | Buechler |
| 6,124,137 A | 9/2000 | Hutchens et al. |
| 6,143,576 A | 11/2000 | Buechler |
| 6,204,500 B1 | 3/2001 | Whitehouse et al. |
| 6,225,047 B1 | 5/2001 | Hutchens et al. |
| 6,235,241 B1 | 5/2001 | Catt et al. |
| 6,268,144 B1 | 7/2001 | Koster |
| 6,329,209 B1 | 12/2001 | Wagner et al. |
| 6,399,398 B1 | 6/2002 | Cunningham et al. |
| 6,780,645 B2 | 8/2004 | Hayter et al. |
| 7,045,366 B2 | 5/2006 | Huang et al. |
| 7,057,165 B2 | 6/2006 | Koopman et al. |
| 7,476,724 B2 | 1/2009 | Dennis et al. |

(Continued)

FOREIGN PATENT DOCUMENTS

| WO | 2005/003154 A2 | 2/2001 |
|---|---|---|
| WO | 2005/052593 A1 | 6/2005 |

(Continued)

OTHER PUBLICATIONS

Waiker et al (J Am Soc Nephrol. Jan. 2012; 23(1): 13-21).*
Christ-Crain et al (Critical Care 2010, 14:203).*
Rosenbaum et al (Clinical Medicine Insights: Therapeutics 2015:7, 33-42).*
Agrawal (Ed.), Protocols for Oligonucleotides and Analogs, Synthesis and Properties, 1993, vol. 20, Humana Press Inc., NJ (Table of Contents).
Atherton et al. (Eds.), Solid Phase Synthesis: a practical approach, 1989, IRL Oxford Press, Oxford, England (Table of Contents).
Bartlett, Clin. Infect. Dis., 2004, 170-172, 39(2).

(Continued)

*Primary Examiner* — Brian Gangle
*Assistant Examiner* — Andrea K McCollum
(74) *Attorney, Agent, or Firm* — Carol L. Francis; Bozicevic, Field & Francis LLP

(57) ABSTRACT

Ghrelin signal peptide fragment assays and kits useful in the diagnosis, prognosis, risk stratification, assessing, staging, monitoring, categorizing and determination of further diagnoses and treatment regimens in subjects with various disorders, diseases and conditions including, pneumonia, heart failure, or pneumonia and heart failure or suspected pneumonia, heart failure, or pneumonia and heart failure, and methods for monitoring treatment.

24 Claims, 7 Drawing Sheets

Specification includes a Sequence Listing.

(56) References Cited

U.S. PATENT DOCUMENTS

| | | | |
|---|---|---|---|
| 8,298,772 | B2 | 10/2012 | Pemberton et al. |
| 8,507,209 | B2 * | 8/2013 | Pemberton et al. ........... 435/7.1 |
| 2003/0054494 | A1 | 3/2003 | Desauvage et al. |
| 2003/0083251 | A1 | 5/2003 | Westenfelder |
| 2004/0157293 | A1 | 8/2004 | Evans et al. |
| 2005/0064511 | A1 | 3/2005 | Buechler et al. |
| 2005/0244902 | A1 | 11/2005 | Gotze et al. |
| 2005/0244904 | A1 | 11/2005 | Ng |
| 2006/0234315 | A1 | 10/2006 | MacFadyen et al. |
| 2008/0312179 | A1 | 12/2008 | Pecker |

FOREIGN PATENT DOCUMENTS

| | | |
|---|---|---|
| WO | 2006/007667 A1 | 1/2006 |
| WO | 2006/131529 A1 | 12/2006 |
| WO | 2009/004315 A1 | 1/2009 |

OTHER PUBLICATIONS

Bowie et al., Science, 1990, 1306-1310, 247(4948).
Brennan et al., Science, 1985, 81-83, 229(4708).
Centers for Disease Control and Prevention, Pneumonia FastStats Sheet, Jan. 2012.
Clackson et al., Nature, 1991, 624-628, 352(6336).
Coligan et al.(Eds.), Current Protocols in Immunology vol. 1, 1991, Wiley-Interscience, New York, NY, USA (Table of Contents Only).
Cwirla et al., Proc. Natl. Acad. Sci. USA, 1990, 6378-6382, 87(16).
Deutscher (Ed.), Methods in Enzymology, 1990, 182 (Table of Contents).
Devlin et al., Science, 1990, 404-406, 249(4967).
Evertsen et al., Prim. Care Resp. J., 2010, 237-241, 19(3).
Fischer et al., Intensive Care Med., 2003, 1043-1051, 29(7).
Freshney (Ed.), Culture of Animal Cells, 2nd Ed., 1987, Alan R. Liss, Inc., NY (Table of Contents).
Gait (Ed.), Oligonucleotide Synthesis: A Practical Approach, 1984, IPL Press, Oxford, Washington DC (Table of Contents).
Garcia et al. Ghrelin and Cardiovascular health, Curr. Opin. Pharmacol., 2006, 142-147, 6(2).
Gennis et al., J. Emerrg. Med., 1989, 263-268, 7(3).
Harlow et al. (Eds.), Antibodies, A Laboratory Manual, 1988, 92-117, Ch. 5, Cold Spring Harbor Publications, NY.
Harlow et al. (Ed.), Using Antibodies: A Laboratory Manual, 1999, Cold Spring Harbor Publications, NY (Table of Contents).
Hermanson (Ed.), Bioconjugate Techniques, 1996, Academic Press, San Diego, CA (Table of Contents).
Hindiyeh et al., Am. J. Clin. Pathol., 2001, 218-224, 116(2).
Holliger et al., Proc. Natl. Acad. Sci. USA. 1993, 6444-6448, 90(14).
Hunt et al., Clin. Endocrinol., 1997, 287-296, 47(3).
Jones et al., Nature, 1986, 522-525, 321(6069).
Klee, Clin. Lab. Med., 2004, 1-18, 24(1).
Kohler et al, Nature, 1975, 495-497, 256(5517).
Kunkel, Proc. Natl. Acad. Sci. USA, 1985, 488-492, 82(2).
Lutz et al., Exp. Cell. Res., 1988, 109-124, 175(1).
Mandell, Infect. Dis. Clin. North Am., 2004, 761-776, 18(4).
Matteucci et al., J. Am. Chem. Soc., 1981, 3185-3191, 103(11).
Merrifield, J. Am. Chem. Soc. 1963, 2149-2154, 85(14).
Miller et al. (Eds.), Gene Transfer Vectors for Mammalian Cells, 1987, Cold Springs Harbor, NY (Table of Contents).
Morrison et al., Proc. Natl. Acad. Sci. USA, 1984, 6851-6855 81(21).
Mullis et al. (Eds.), The Polymerase Chain Reaction, 1994, Birkhauser (Table of Contents).
Munson et al., Anal. Biochem., 1980, 220-239, 107(1).
Murdoch et al., J. Clin. Micro., 2009, 3405-3408, 47(11).
Nelson et al., Comput. Methods Programs Biomed., 1988, 65-68, 27(1).
Ng et al., J. Cell Mol. Med., 2002, 329-340, 6(3).
Paul (Ed.), Fundamental Immunology, 2nd ed., 1989, Raven Press, NY (Table of Contents).
Pluckthun, inRosenburg et al. (Eds.), The Pharmacology of Monoclonal Antibodies, 1994, 113, 269-315, Ch. 11, Springer-Verlag.
Riechmann et al., Nature, 1988, 323-327, 332(6162).
Sambrook et al. (Eds.), Molecular Cloning: A Laboratory Manual, 2nd Ed., 1989, Cold Spring Harbor Press (Table of Contents).
Schuetz et al., Swiss Med. Wkly., 2009, 318-326, 139(23-24).
Scopes (Ed.), Protein Purification: Principles and Practice, 1987, Springer-Verlag, NY (Table of Contents).
Scott et al., Science, 1990, 386-390, 249(4967).
Sharma et al., Curr. Opin. Pulm. Med., 2007, 159-169, 13(3).
Stewart (Ed.), Solid-Phase Peptide Synthesis, 1969, WH Freeman Co., San Francisco, CA (Table of Contents).
Summah et al., Biomarkers: A Definite Plus in Pneumonia, Mediators Inflamm. 2009, 675753, 1-9.
Suresh et al., Methods Enzymol., 1986, 210-228, 121.
Van Erp et al., J. Immunoassay, 1991, 425-443, 12(3).
Walker (Ed.), Protein Protocols Handbook, 2nd Ed., 2002, Humana Press, Totowa, NJ (Table of Contents).
Ward et al., Nature, 1989, 544-546, 341(6242).
Weir (Ed.), Handbook of Experimental Immunology, 4th Ed., 1986, vol. 1, Blackwell Scientific Publications, Oxford (Table of Contents).
Werno et al., Laboratory diagnosis of invasive pneumococcal disease, Clin. Infect. Dis., 2008, 926-932, 46(6).
Wild (Ed.), The Immunoassay Handbook, 3rd Ed., 2005, 103, 121-126, Elsevier Ltd.
Wilson et al., J. Immunol. Methods, 1994, 267-273, 175(2).
Yarmush et al., J. Biochem. Biophys. Methods, 1992, 285-297, 25(4).
Zapata et al., Protein Eng., 1995, 1057-1062, 8(10).
Zola (Ed.), Monoclonal Antibodies: A Manual of Techniques, 1987, 147-158, CRC Press, Inc.
Reyzer et al., MALDI Mass Spectrometry for Direct Tissue Analysis: A New Tool for Biomarker Discovery, J. Proteome Res., 2005, 1138-1142, 4(4).
Rice et al., EMBOSS: The European Molecular Biology Open Software Suite, Trends Genet., 2000, 276-277, 16(6).
Richards et al., Plasma N-terminal pro-brain natriuretic peptide and adrenomedullin: new neurohormonal predictors of left ventricular function and prognosis after myocardial infarction, Circulation, 1998, 1921-1929, 97(19).
Richards et al., Antecedent hypertension and heart failure after myocardial infarction, J. Am. Coll. Cardiol., 2002, 1182-1188, 39(7).
Ronco et al., Cardiorenal Syndrome, J. Am. Coll. Cardiol., 2008, 1527-1539, 52(19).
Skowera et al., CTLs are targeted to kill beta cells in patients with type 1 diabetes through recognition of a glucose-regulated preproinsulin epitope, J. Clin. Invest., 2008, 3390-3402, 118(10).
Skyler, Non-insulin-dependent diabetes mellitus: a clinical strategy, Diabetes Care, 1984, 118-129, Suppl. 1.
Solberg, Approved recommendation on the theory of reference values, Part 5, Statistical treatment of collected reference values, Determination of reference limits, J. Clin. Chem. Clin. Biochem., 1987, 645-656, 25.
Squire et al., N-terminal pro-atrial natriuretic peptide (N-ANP) and N-terminal pro-B-type natriuretic peptide (N-BNP) in the prediction of death and heart failure in unselected patients following acute myocardial infarction, Clin. Sci. (Lond.), 2004,309-316, 107(3).
Tapanainen et al., Natriuretic peptides as predictors of non-sudden and sudden cardiac death after acute myocardial infarction in the beta-blocking era, J. Am. Coll. Cardiol., 2004, 757-763, 43(5).
Tatusov et al., A Genomic Perspective on Protein Families, Science, 1997, 631-637, 278(5338).
Tatusova et al., BLAST 2 Sequences, a new tool for comparing protein and nucleotide sequences, FEMS Microbiol Lett, 1999, 247-250, 174(2).
Thibault et al., NH2-terminal fragment of rat pro-atrial natriuretic factor in the circulation: identification, radioimmunoassay and half-life, Peptides, 1988, 47-53, 9(1).

(56) References Cited

OTHER PUBLICATIONS

Thomas, Hybridization of denatured RNA and small DNA fragments transferred to nitrocellulose, Proc. Natl., Acad. Sci. USA, 1980, 5201-5205, 77(9).
Thompson et al., CLUSTAL W: improving the sensitivity of progressive multiple sequence alignment through sequence weighting, position-specific gap penalties and weight matrix choice, Nucleic Acids Res., 1994, 4673-4680, 22(22).
Thygesen et al., Universal definition of myocardial infarction, Circulation, 2007, 2634-2653, 116(22).
Toma et al., Recognition of Human Proinsulin Leader Sequence by Class I—Restricted T-Cells in HLA-A*0201 Transgenic Mice and in Human Type 1 Diabetes, Diabetes, 2009, 394-402, 58(2).
Triglia et al., A procedure for in vitro amplification of DNA segments that lie outside the boundaries of known sequences, Nucleic Acids Res., 1998, 8186, 16(16).
Troughton et al., Plasma B-type natriuretic peptide levels in systolic heart failure: Importance of left ventricular diastolic function and right ventricular systolic function, J. Am. Coll. Cardiol., 2004, 416-422, 43(3).
Troughton et al., Treatment of heart failure guided by plasma amino-terminal brain natriuretic peptide (N-BNP) concentrations, Lancet, 2000, 1126-1130, 355(9210).
Vaughn et al., Human antibodies by design, Nat. Biotechnol., 1998, 535-539, 16(6).
Verhoeyen et al., Reshaping human antibodies: grafting an antilysozyme activity, Science, 1988, 1534-1536, 239(4847).
Viljoen et al., Molecular diagnostic PCR handbook, 2005, Springer (Table of Contents).
Waiker et al., Imperfect Gold Standards for Kidney Injury Biomarker Evaluation, J. Am. Soc. Nephrol., 2012, 13-21, 23(1).
Wheeler et al., Laboratory Diagnosis of Invasive Pneumococcal Disease, Nucleic Acids Res., 2001, 11-16, 29(1).
Abbott Press Release, New Point of Care Test Helps Physicians Quickly, Accurately Assess Difficult-to-Diagnose Heart Failure at Patient's Bedside, Jul. 26, 2006, retrieved online Dec. 13, 2007at URL: http://www.abbott.com/global/url/pressRelease/en_US/60.5:5/Press_Release-0339.htm.
Altschul et al., Gapped BLAST and PSI-BLAST: a new generation of protein database search programs, Nucleic Acid Res., 1997, 3389-3402, 25(17).
Antman et al., Acute myocardial infarction, in Braunwald et al. (Eds.), Heart disease: a textbook of cardiovascular medicine, 6th ed., 2001, 1114-1231, vol. 2, Ch. 35.
Apple et al., National Academy of Clinical Biochemistry and IFCC Committee for standardization of markers of cardiac damage laboratory medicine practice guidelines: analytical issues for biochemical markers of acute coronary syndromes, Circulation, 2007, e352-e355, 115(13).
Bairoch et al., PROSITE: recent developments, Nucleic Acids Res., 1994, 3583-3589, 22(17).
Baxevanis, The Molecular Biology Database Collection: an updated compilation of biological database resources, Nucleic Acids Res., 2001, 1-10, 29(1).
Bennet et al., The risk of myocardial infarction is enhanced by a synergistic interaction between serum insulin and smoking, Eur. J. Endocrinol., 641-647, 147(5), (2002).
Bolton et al., A General Method for the Isolation of RNA Complementary to DNA, Proc. Natl. Acad. Sci., 1962, 1390-1397, 48(8).
Braud et al., HLA-E binds to natural killer cell receptors CD94/NKG2A, B and C, Nature, 1998, 795-799, 391(6669).
Chang et al., Novel strategy for identification of candidate cytotoxic T-cell epitopes from human preproinsulin, Tissue Antigens, 2003, 408-417, 62(5).
Chenna et al., Multiple Sequence Alignment with the Clustal series of programs, Nucl. Acids Res., 2003, 3497-3500, 31(13).
Cohen, Nonchromosomal Antibiotic Resistance in Bacteria: Genetic Transformation of *Escherichia coli* by R-Factor DNA, Proc. Natl. Acad. Sci. USA, 1972, 2110-2114, 69(8).
Congia et al., T cell epitopes of insulin defined in HLA-DR4 transgenic mice are derived from preproinsulin and proinsulin, Proc. Natl. Acad. Sci. USA, 1998, 3833-3838, 95(7).
Dale et al. (Eds.), From Genes to Genomes: Concepts and Applications of DNA Technology, Ed. 2, 2007, Wiley, NY (Table of Contents).
Dieguez et al., Ghrelin: a step forward in the understanding of somatroph cell function and growth regulation, Eur. J. Endocrinol., 413-417, 142(5), (2000).
Ducimetiere et al., Relationship of Plasma Insulin Levels to the Incidence of Myocardial Infarction and Coronary Heart Disease Mortality in a Middle-aged Population, Diabetologia, 1980, 205-210, 19(3).
Falquet et al., The PROSITE database, it's status in 2002, Nucleic Acids Res., 2002, 235-238, 30(1).
Feng et al., Progressive sequence alignment as a prerequisitetto correct phylogenetic trees, J. Mol. Evol., 1987, 351-360, 25(4).
Frohman, Rapid amplification of complementary DNA ends for generation of full-length complementary DNAs: Thermal race, Methods Enzymol., 1993, 340-356, 218.
Giesen et al., A formula for thermal stability (Tm) prediction of PNA/DNA duplexes, Nucleic Acids Res., 1998, 5004-5006, 26(21).
Gilchrist et al., Immunoneutralization of Growth Differentiation Factor 9 Reveals It Partially Accounts for Mouse Oocyte Mitogenic Activity, Biology and Reproduction, 2004, 732-739, 71(3).
Golemis (Ed.), Protein-protein Interactions: A Molecular Cloning Manual, 2002, Cold Springs Harbor, NY (Table of Contents).
Gutierrez-Marcos et al., Atrial natriuretic peptide in patients with accute myocardial infacrtion without functional heart failure, Eur. Heart J., 1991, 503-507, 12(4).
Hess et al., N-terminal pro-brain natriuretic peptide (NT-proBNP) in healthy blood donors and in patients from general practitioners with and without a diagnosis of cardiac arrest, Clin. Lab. 2005, 167-172, 51(3-4), Pubmed Abstract PMID 15819172.
Hofmann et al., The PROSITE database, it's status in 1999, Nucleic Acids Res., 1999, 215-219, 27(1).
Hofmann, Gene Expression Profiling by Microarrays: Clinical Implications, 2006, Cambridge University Press (Table of Contents).
Hoogenboom et al., Human antibodies from synthetic repertoires of germline VH gene segments rearranged in vitro, J. Mol. Biol., 1992, 381-388, 227(2).
Howard et al. (Eds.), Making and Using Antibodies: A Practical Handbook, 2007, CRC Press (Table of Contents).
Huang, On Global Sequence Alignment, Comput. Appl. Biosci., 1994, 227-235, 10(3).
Jain, Current Status of Fluorescent In Situ Hybridization, Med. Device Technol., 2004, 14-17, 15(4).
Jernberg et al. N-terminal pro Brain Natriuretic Peptide on admission for early risk stratification of patients with chest pain and no ST-segment elevation, J. Am. Coll. Cardiol., 2002, 437-445, 40(3).
Jung et al., Elevated concentrations of cardiac troponins are associated with severe coronary artery calcification in asymptomatic haemodialysis patients, Nephrol. Dial. Transplant, 2004, 3117-3123, 19(12).
Lindahl et al., High Proinsulin Concentration Precedes Acute Myocardial Infarction in a Nondiabetic Population, Metabolism, 1197-1202, 48, (1999).
Lundblad (Ed.), Techniques in Protein Modification Edition: 2, 1995, CRC Press, (Table of Contents).
Martoglio et al., Signal sequences: more than just greasy peptides, Trends Cell. Biol., 410-415, 8(10), (1998).
Mehra et al., Usefulness of elevated B-type natriuretic peptide to predict allograft failure, cardiac allograft vasculopathy and survival after heart transplant, Am. J. Cardiol. 2004, 454-458, 94(4), Pubmed Abstract PMID 15325298.
Milstein et al., Hybrid hybridomas and their use in immunohistochemistry, Nature, 1983,537-539, 305(5934).
Muller et al. (Eds.), Microarray Technology and its Application, 2005, Springer (Table of Contents).
Naghavi et al., From Vulnerable Plaque to Vulnerable Patient : A Call for New Definitions and Risk Assessment Strategies: Part I, Circulation, 2003, 1664-1672, 108(14).

(56) References Cited

OTHER PUBLICATIONS

Needlemen et al., A General Method Applicable to the Search for Similarities in the Amino Acid Sequence of Two Proteins, J. Mal. Biol., 1970, 443-453, 48.

Neuberger, Generating high-avidity human Mabs in mice, Nat. Biotechnol., 1996, 826, 14(7).

Nielsen et al., Sequence-Selective Recognition of DNA by Strand Displacement with a Thymine-Substituted Polyamide, Science, 1991, 1497-1500, 254(5037).

NIH Guide, Molecular and Physical Characterization of the Vulnerable Plaque, 1997, 26(37).

Notredame et al., T-Coffee: A Novel Method for Fast and Accurate Multiple Sequence Alignment, J. Mol. Biol., 2002, 205-217, 302(1).

Omland et al., Plasma brain natriuretic peptide as an indicator of left ventricular systolic function and long-term survival after acute myocardial infarction. Comparison with plasma atrial natriuretic peptide and N-terminal proatrial natriuretic peptide, Circulation, 1996, 1963-1969, 93(11).

Omland et al., N-Terminal pro-B type natriuretic peptide and long-term mortality in acute coronary syndromes, Circulation, 2002, 2913-2918, 106(23).

Pemberton et al., Deconvolution Analysis of Cardiac Natriuretic Peptides During Acute Volume Overload, Hypertension, 2000, 355-359, 36(3).

Poykko et al., Low plasma ghrelin is associated with insulin resistance, hypertension, and the prevalence of type 2 diabetes, Diabetes, 2003, 2546-2553, 52(10).

Raju et al., T Cell Recognition of Human Pre-Proinsulin Peptides Depends on the Polymorphism at HLA DQ Locus: A Study Using HLA DQ8 and DQ6 Transgenic Mice, Hum. Immunol., 1997, 21-29, 58(1).

Huston et al., Protein engineering of antibody binding sites: Recovery of specific activity in an anti-digoxin single-chain Fv analogue produced in *Escherichia coli*, Proc. Natl. Acad. Sci. USA, 1988, 5879-5883, 85(16).

\* cited by examiner

Figure 2

```
Rattus norvegicus         MVSSATICSLLLLSMLWM-DMAMA
Homo sapiens              MPSPGTVCSLLLLGMLWL-DLAMA
Ovis aries                MPAPRTIYSLLLLSLLWM-DLAMA
Sus scrofa                MPSTGTICSLLLLSVLLMADLAMA
Mus musculus              MLSSGTICSLLLLSMLWM-DMAMA
Canis lupus familiaris    MPSLGTMCSLLLFSVLWV-DLAMA
Felis catus               MPSPGTVCSLLLFSMLWA-DLAMA Consensus                 MPSPGTICSLLLLSMLWMADLAMA
```

Figure 3

| Peptide | Cross reactivity with Ghr-SPn(1-9) antiserum (%) |
| --- | --- |
| Ghr-SPn(1-9) | 100 |
| proBNP(1-13) | <0.003 |
| proBNP(1-76) | <0.01 |
| proANP(1-30) | <0.009 |
| Insulin | <0.003 |
| IGF-I | <0.002 |
| IGF-II | <0.006 |
| ANP | <0.008 |
| BNP | <0.009 |
| Endothelin 1 | <0.006 |
| Angiotensin II | <0.003 |
| Angiotensin(1-7) | <0.01 |
| Urotensin II | <0.003 |
| CNP | <0.006 |
| Ghrelin | <0.007 |
| C-Ghrelin | <0.01 |
| proCNP(1-15) | <0.008 |
| Adrenomedullin | <0.01 |
| Urocortin I | <0.01 |
| Urocortin II | <0.01 |
| BNP-SPn(1-10) | <0.001 |
| ANP-SPc(16-25) | <0.001 |
| ANP-SPn(1-10) | <0.001 |
| INS-SPn(1-9) | <0.001 |
| Clopidigrel | 0 |
| Morphine | 0 |
| Aspirin | 0 |

BIOMARKERS FOR PNEUMONIA AND ACUTE DECOMPENSATED HEART FAILURE

RELATED APPLICATION

This application claims the benefit of and priority to U.S. provisional patent application Ser. No. 61/613,311, filed 20 Mar. 2012, the contents of which is hereby incorporated by reference in its entirety for any and all purposes.

FIELD

The present invention relates to ghrelin signal peptide fragment biomarkers. It also relates to ghrelin signal peptide fragment biomarker methods and kits and their use, for example, in the prognosis, diagnosis and monitoring of pneumonia infections, heart failure or pneumonia and heart failure, and related biological events or states that result in release of the peptide fragments into the circulation.

BACKGROUND

The following includes information that may be useful in understanding the present invention. It is not an admission that any of the information, publications or documents specifically or implicitly referenced herein is prior art, or essential, to the presently described or claimed inventions. All publications and patents mentioned herein are hereby incorporated herein by reference in their entirety.

Patients presenting to hospital emergency departments with breathlessness (dyspnea) as the primary complaint can have multiple causes for their condition. Breathlessness may be caused by cardiac, lung, pulmonary, non-cardiopulmonary or infectious disorders (alone or in combination) and it is important that timely and accurate diagnosis is made. Differential diagnosis strategies to address this focus on clinical workup, patient history and invasive/non-invasive test results.

With respect to the infectious diseases, pneumonia represents a significant challenge in terms of rapid diagnosis and patient numbers and there are limited biomarker options available to the clinician.

Pneumonia is a form of acute respiratory infection, which is caused by several bacterial, viral and fungal pathogens including *Streptococcus pneumoniae, Haemophilus influenzae* type b, Respiratory Syncytial Virus and in patients with HIV, *Pneumocystis jiroveci*. The resulting infection is characterised by inflammation of alveoli and an accumulation of fluid in the lungs. Symptoms of pneumonia include difficulty in breathing, increased respiratory rate, cough, fever, chills and chest pain.

Pneumonia has a high morbidity and mortality rate. Sharma S, et al., Radiological imaging in pneumonia: recent innovations. *Current Opinion in Pulmonary Medicine.* 2007; 13(3):159-169. It is recognized as a significant cause of morbidity and mortality worldwide, exceeding that of HIV, malaria and measles combined (UNICEF; Pneumonia: the forgotten killer of children. 2006; UNICEF/WHO, Geneva, Switzerland). Every year, pneumonia kills an estimated 1.8 million children under the age of five years, accounting for 20% of all deaths in this age group and accounting for four paediatric deaths per minute (WHO Fact Sheet No. 331, October 2011). Pneumonia incidence has been found to be closely interrelated to health inequalities with the highest prevalence in South Asia and sub-Saharan Africa.

In the United States, more than 3 million people develop pneumonia each year. Of these approximately 20% require hospitalization with an average length of stay of 5.2 days and an average admission rate of 1.17 per patient. Pneumonia accounts for 3.4% of all inpatient deaths equating to a mortality rate of 16.5 per 100,000 population (Centres for Disease Control and Prevention, Pneumonia FastStats Sheet, January 2012). In addition to the burden imposed by pneumonia in the in-patient setting, community-acquired pneumonia results in more than 10 million visits to primary care physicians and 64 million days of restricted activity per annum (Mandell L. A. Epidemiology and etiology of community-acquired Pneumonia, *Infect Dis Clin North Am.* 2004; 18(4):761-76).

Clinical diagnosis of Pneumonia is complicated by the fact that symptoms are not reliably predictive. In a study of 308 patients presenting to an emergency department cough was the most common symptom in patients with pneumonia (86%), but was equally common in those with other respiratory illness. Fever was absent in 31% of patients with pneumonia, abnormal findings on lung examination were found in less than 50% of the patients with pneumonia, whilst abnormal vital signs (temperature greater than 37.8 degrees C. (100 degrees F.), pulse greater than 100/min, or respirations greater than 20/min) were the best predictor, reported in 97% of patients with pneumonia. Gennis P., et al., Clinical criteria for the detection of Pneumonia in adults: guidelines for ordering chest roentgenograms in the emergency department. *J Emrg Med,* 1989; 7(3):263-8.

Based on current American Thoracic Society and Infectious Diseases Society of America guidelines, the gold standard for differentiation of pneumonia from acute bronchitis in patients presenting to emergency departments is the presence of lung infiltrates indicated by a chest radiograph. However chest x-ray results are an inconsistent predictor, due to variability in interpretation, and are unable to establish the causative pathogen. In addition patients presenting with community-acquired pneumonia in an out-patient setting may not get a chest x-ray due to limited accessibility and cost. Evertsen J., et al., Diagnosis and management of Pneumonia and bronchitis in outpatient primary care practices, *Primary Care Resp J,* 2010; 19(3):237:241.

Due to the difficulties in accurate clinical diagnosis, laboratory diagnostics are frequently utilized by physicians to assist in differentiating pneumonia from Acute Respiratory Tract Infection (ARTI), and to identify the causative pathogen to ascertain the most appropriate treatment. Laboratory diagnostics include microscopy and culture of lower respiratory tract specimens, blood cultures, detection of antigens in urine, and serology. Bartlett, J. G., Decline in microbial studies for patients with pulmonary infections, *Clin. Infect. Dis.* 2004; 39; 170-172. The last several years new diagnostics in the areas of antigen and nucleic acid detection have emerged, and commercial antigen detection assays are now available for several pneumonia pathogens, particularly *S. pneumoniae, Legionella pneumophila,* and some respiratory viruses. A new generation of immunochromatographic pneumococcal urinary antigen tests that detect the C-polysaccharide cell wall antigen have proven useful for diagnosing pneumococcal pneumonia in adults (Werno, A. M., et al., Laboratory diagnosis of invasive pneumococcal disease, *Clin. Infect. Dis.* 2008; 46: 926-932). Several commercial rapid-result tests, using immunochromatography, enzyme-linked immunosorbent assay, or other formats, are now available for respiratory viruses, including influenza and respiratory syncytial viruses, assisting in the differentiation of ARTI and influenza from pneumonia.

Nucleic acid detection tests (NATs), such as PCR, have also been developed for the major pneumonial pathogens, and are available as multiplex platforms. NATs are able to detect very low levels of nucleic acid from respiratory pathogens, do not depend on the viability of the target microbe, and can provide information on the presence of antibiotic resistance phenotypes. Murdoch D. R., et al., Breathing New Life into Pneumonia Diagnostics, *J of Clin Micro,* 2009; 47(11):3405-3408). Despite the high level of sensitivity and specificity exhibited by NATs, their commercial uptake has been limited by their cost and time required to run the test. Hindiyeh, M., et al., Evaluation of the Prodesse Hexaplex multiplex PCR assay for direct detection of seven respiratory viruses in clinical specimens, *Am. J. Clin. Pathol.* 2001; 116:218-224.

In sum, very often, clinical signs of pneumonia can be very elusive. At the heart of the dilemma, the question remains: "what is the fastest way to come to the correct diagnosis?" Because the faster the diagnosis is reached, the earlier the treatment begins. However, there is almost always a large lapse of time between the time of onset of symptoms and the start antibiotic therapy due to delayed diagnosis. In an attempt to achieve the rapid diagnosis of pneumonia and shortened antibiotic courses, the use of biomarkers is now being contemplated.

Physicians are becoming more and more interested in the use of biomarkers since there is no "gold standard" which is both sensitive and specific enough to help them reach the "correct" diagnosis for pneumonia. A "correct" diagnosis would be one in which the causative pathogen can be identified morphologically. However, 70% of patients with radiologically confirmed community-acquired pneumonia (CAP) do not have the causative organism identified. Some of the biomarkers which are at the offing as an adjunct in the diagnosis of pneumonia include C-reactive protein, leukocyte count, immunoglobulins, and proinflammatory cytokines. There are other biomarkers whose importance is growing, namely procalcitonin (PCT) and Triggering receptor expressed on myeloid cells-1 (TREM-1). Still other possible biomarkers being studied for their possible use in pneumonia include copeptin, cortisol, endotoxin, proadrenomedullin, amongst others. Hanssa Summah and Jie-Ming Qu, Biomarkers: A Definite Plus in Pneumonia, *Mediators Inflamm.* 2009: 675753 (Published online 2009 Nov. 16).

Chronic stable heart failure may easily decompensate leading to acute decompensated heart failure (ADHF). ADHF is a worsening of the symptoms, typically shortness of breath (dyspnea), edema and fatigue, in a patient with existing heart disease. It is a common and potentially serious cause of acute respiratory distress, and its most sensitive clinical sign is jugular venous distension. Brain natriuretic peptide (BNP) is a well documented and used biomarker for the diagnosis of ADHF, where elevated levels in blood relative to a control or reference level is diagnostic of this condition.

The accurate and rapid detection of acute decompensated heart failure (ADHF) or pneumonia as the cause for breathlessness is an important and large time consuming problem for emergency department doctors or general practitioners. This is because inaccurate or incomplete diagnosis coupled with resultant incorrect treatment can be fatal, due to incorrect treatment or time delays to instituting correct treatment.

There are currently no accepted or regularly used biomarkers for the detection of pneumonia. Furthermore, there is no single marker or panel of biomarkers that can diagnose whether a patient has ADHF and pneumonia. This is vitally important as the diagnosis of pneumonia is often missed in patients with diagnosed ADHF, a situation which severely compromises the effective treatment of such patients, and can prove fatal.

Human ghrelin signal peptide (GHRsp) is a 23 amino acid peptide cleaved from ghrelin (preproghrelin) (1-117) (SEQ ID NO:1). Processing of human preproghrelin is shown in FIG. 1. Human GHRsp (1-23) is shown separately in SEQ ID NO:2. U.S. patent application Ser. No. 12/922,444 (Publication No. 20110008808) describes and claims binding agents and assays for ghrelin signal peptides and fragments, including GHRsp (1-9) (SEQ ID No:3), which are reported to be useful in methods for predicting, diagnosing, assessing or monitoring acute cardiac disorders, glucose handling disorders, and diabetes in a subject.

Importantly, for example, Applicants have discovered that ghrelin signal peptide fragments are a new and reliable biomarker for pneumonia, as well as a new and reliable biomarker for acute decompensated heart failure and as a new and reliable biomarker for patients who have both pneumonia and acute decompensated heart failure.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

Applicants made the discovery that ghrelin signal peptide (GHRsp) fragments are detectably released into the circulation in response to pneumonia infection. In a subject with pneumonia, GHRsp fragment levels are different than normal. GHRsp (1-9) (SEQ ID NO:3) or GHRsp (1-10) (SEQ ID NO: 4) or both are useful as markers for this condition.

Applicants have also made the discovery that GHRsp fragments are detectably released into the circulation in response to acute decompensated heart failure (ADHF) and in response to a circumstance where both pneumonia and ADHF are present. In a subject with ADHF or pneumonia and ADHF, for example, GHRsp fragment levels are different than normal. GHRsp (1-9) (SEQ ID NO:3) or GHRsp (1-10) (SEQ ID NO: 4) or both are useful as markers for either condition.

It is an object of the invention to provide methods and compositions for evaluating pneumonia or suspected infection in a subject. As described herein, measurement of one or more GHRsp fragment markers selected from the group consisting of GHRsp (1-9) (SEQ ID NO:3) or GHRsp (1-10) (SEQ ID NO:4), for example, can be used for diagnosis, prognosis, risk stratification, assessing, staging, monitoring, categorizing and determination of further diagnosis and treatment regimens in subjects with pneumonia or suspected pneumonia.

It is also an object of the present invention to provide methods and compositions for evaluating ADHF or suspected ADHF, or in evaluating pneumonia and ADHF or suspected pneumonia and ADHF, in a subject. As described herein, measurement of one or more GHRsp fragment markers selected from the group consisting of GHRsp (1-9) (SEQ ID NO:3) or GHRsp (1-10) (SEQ ID NO:4), for example, can be used for diagnosis, prognosis, risk stratification, assessing, staging, monitoring, categorizing and determination of further diagnosis and treatment regimens in subjects with ADHF or suspected ADHF, or with pneumonia and ADHF or suspected pneumonia and ADHF.

The invention also provides a GHRsp fragment biomarker assay for use in diagnosing, assessing or monitoring pneumonia, acute decompensated heart failure, or pneumonia and acute decompensated heart failure in a subject.

Applicants provide in one aspect of their invention a method for diagnosis, prognosis, risk stratification, assessing, staging, monitoring, categorizing and determination of further diagnosis and treatment regimens in subjects with pneumonia or suspected pneumonia, acute decompensated heart failure or suspected acute decompensated heart failure, pneumonia and acute decompensated heart failure or suspected pneumonia and acute decompensated heart failure, the method comprising measuring the level of one or more GHRsp fragment biomarkers in one or more samples taken or derived from the subject.

Accordingly, the invention also provides a biomarker assay for pneumonia, acute decompensated heart failure (ADHF) or pneumonia and acute decompensated heart failure (ADHF) comprising detecting and measuring the level of a GHRsp fragment in a biological sample or sample derivative from a subject using any known methods in order to determine the presence or status of a pneumonia infection in the subject, or of ADHF in the subject, or of pneumonia and ADHF in the subject, including diagnosis, prognosis, risk stratification, assessing, staging, monitoring, categorizing and determination of further diagnosis and treatment regimens in subjects with pneumonia or suspected pneumonia, ADHF or suspected ADHF, or pneumonia and ADHF or suspected pneumonia and ADHF.

The invention also provides an assay for a GHRsp fragment biomarker in diagnosing, evaluating or monitoring pneumonia in a subject with pneumonia or suspected pneumonia, comprising:
(a) binding one or more GHRsp fragment biomarkers from a sample;
(b) measuring the level of bound GHRsp fragment biomarker; and
(c) correlating said measurement with known GHRsp fragment values to diagnose, prognose, risk stratify, assess, stage, monitor, categorize, and/or determine the use of further diagnostic techniques and/or treatment regimens in subjects with pneumonia or suspected pneumonia. The GHRsp fragment biomarker may be bound using any GHRsp fragment-specific binding agent.

The invention also provides an assay for a GHRsp fragment biomarker in diagnosing, evaluating or monitoring acute decompensated heart failure (ADHF) in a subject with ADHF or suspected ADHF, comprising:
(a) binding one or more GHRsp fragment biomarkers from a sample;
(b) measuring the level of bound GHRsp fragment biomarker; and
(c) correlating said measurement with known GHRsp fragment values to diagnose, prognose, risk stratify, assess, stage, monitor, categorize, and/or determine the use of further diagnostic techniques and/or treatment regimens in subjects with ADHF or suspected ADHF. The GHRsp fragment biomarker may be bound using any GHRsp fragment-specific binding agent.

The invention further provides an assay for a GHRsp fragment biomarker in diagnosing, evaluating or monitoring pneumonia and acute decompensated heart failure (ADHF) in a subject with pneumonia and ADHF or suspected pneumonia and ADHF, comprising:
(a) binding one or more GHRsp fragment biomarkers from a sample;
(b) measuring the level of bound GHRsp fragment biomarker; and
(c) correlating said measurement with known GHRsp fragment values to diagnose, prognose, risk stratify, assess, stage, monitor, categorize, and/or determine the use of further diagnostic techniques and/or treatment regimens in subjects with pneumonia and ADHF or suspected pneumonia and ADHF. The GHRsp fragment biomarker may be bound using any GHRsp fragment-specific binding agent.

In one embodiment, the GHRsp fragment biomarker is GHRsp (1-9) (SEQ ID NO:3). In one embodiment, the GHRsp fragment biomarker is GHRsp (1-10) (SEQ ID NO:4). In another embodiment, the GHRsp fragment biomarker is GHRsp (1-9) (SEQ ID NO:3) and GHRsp (1-10) (SEQ ID NO:4).

In another aspect, the level of the one or more GHRsp fragment biomarkers are analyzed in conjunction with a reference value or range for said one or more biomarkers, e.g., a normal (non-infected) reference value or range.

In another aspect, the method comprises comparing the level of a GHRsp fragment biomarker in one or more samples taken or derived from the subject with the GHRsp fragment biomarker level from a control wherein a deviation in the measured level from the control level is indicative of pneumonia. Deviations from normal (non-infected) control subjects may be about 10-20%, 10-20%, 10-30%, 10-40%, 10-50%, 10-60%, 10-70%, 10-80%, 10-900%, 10-100%, or higher.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a GHRsp fragment marker measured in such normal subjects. Alternatively, the threshold value may be determined from a "diseased" population of subjects, e.g., those suffering from pneumonia, acute decompensated heart failure (ADHF) or pneumonia and ADHF by selecting a concentration representing the $75^{th}$, $85^{th}$, $90^{th}$, $95^{th}$, or $99^{th}$ percentile of a GHRsp fragment marker measured in such subjects. In another alternative, the threshold value may be determined from a prior measurement of a GHRsp fragment marker in the same subject; that is, a temporal change in the level of a GHRsp fragment marker in the subject may be used to assign risk to the subject.

The foregoing discussion is not meant to imply, however, that the GHRsp fragment markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

Multiple thresholds may also be used to assess pneumonia in a subject. For example, a first subpopulation which is infected (e.g. with pneumonia) and/or affected (e.g. with heart failure) and a second subpopulation which is not infected and/or affected can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to be infected in comparison to someone in the first tertile. The third tertile is also assigned an odds ratio that is relative to that first tertile.

The ability of a particular test to distinguish two populations can be established using ROC analysis. For example, ROC curves established from a first subpopulation which is infected with pneumonia and a second subpopulation which is not infected can be used to calculate a ROC curve, and the area under the curve provides a measure of the quality of the test. Preferably, the tests described herein provide a ROC curve area greater than 0.5, preferably at least 0.6, and more preferably at least 0.7. The same analysis applies to a subject affected by acute decompensated heart failure (ADHF) or infected and affected with both pneumonia and ADHF.

Applicants have also surprisingly discovered that the circulating concentration of GHRsp fragment biomarkers is highest in the 48-72 following onset of symptoms consistent with clinical presentation of pneumonia, acute decompensated heart failure (ADHF) or pneumonia and ADHF. Peaks are in the order of, for example, 1-2 times higher, commonly at least 50% times higher, than normal control populations at this time.

Accordingly, in a further aspect the present invention provides a method for predicting, assessing, diagnosing, categorizing or monitoring the severity of pneumonia in a subject, the method comprising measuring the level of a GHRsp fragment biomarker in a biological sample from the subject and comparing the level of said GHRsp fragment biomarker with the GHRsp and/or GHRsp fragment level from a control or reference value or value range wherein a measured level of the GHRsp fragment biomarker at multiples greater than the control level or predetermined reference value or value range is indicative of the severity of pneumonia in the subject.

In another aspect the present invention provides a method for predicting, assessing, diagnosing, categorizing or monitoring the severity of acute decompensated heart failure (ADHF) in a subject, the method comprising measuring the level of a GHRsp fragment biomarker in a biological sample from the subject and comparing the level of said GHRsp fragment biomarker with the GHRsp and/or GHRsp fragment level from a control or reference value or value range wherein a measured level of the GHRsp fragment biomarker at multiples greater than the control level or predetermined reference value or value range is indicative of the severity of ADHF in the subject.

In yet another aspect the present invention provides a method for predicting, assessing, diagnosing, categorizing or monitoring the severity of pneumonia and acute decompensated heart failure (ADHF) in a subject, the method comprising measuring the level of a GHRsp fragment biomarker in a biological sample from the subject and comparing the level of said GHRsp fragment biomarker with the GHRsp and/or GHRsp fragment level from a control or reference value or value range wherein a measured level of the GHRsp fragment biomarker at multiples greater than the control level or predetermined reference value or value range is indicative of the severity of pneumonia and ADHF in the subject.

The GHRsp fragment biomarker is, for example, GHRsp (1-9) (SEQ ID NO:3) or GHRsp (1-10) (SEQ ID NO:4).

The invention also provides a method for monitoring a response to treatment of pneumonia in a subject, the method comprising measuring the level of a GHRsp fragment biomarker in a sample taken or derived from the subject and comparing the level of said GHRsp fragment biomarker with the GHRsp fragment biomarker level from a control or a reference value or value range, wherein a change in the measured level of GHRsp from the control level, or a predetermined reference value or value range, is indicative of a response to the treatment.

The invention further provides a method for monitoring a response to treatment of acute decompensated heart failure (ADHF) in a subject, the method comprising measuring the level of a GHRsp fragment biomarker in a sample taken or derived from the subject and comparing the level of said GHRsp fragment biomarker with the GHRsp fragment biomarker level from a control or a reference value or value range, wherein a change in the measured level of GHRsp from the control level, or a predetermined reference value or value range, is indicative of a response to the treatment.

The invention further provides a method for monitoring a response to treatment of pneumonia and acute decompensated heart failure in a subject, the method comprising measuring the level of a GHRsp fragment biomarker in a sample taken or derived from the subject and comparing the level of said GHRsp fragment biomarker with the GHRsp fragment biomarker level from a control or a reference value or value range, wherein a change in the measured level of GHRsp from the control level, or a predetermined reference value or value range, is indicative of a response to the treatment.

Again, the GHRsp fragment biomarker is, for example, GHRsp (1-9) (SEQ ID NO:3) or GHRsp (1-10) (SEQ ID NO:4).

In one embodiment of the methods of the invention the GHRsp fragment biomarker level is measured two or more times on samples (or sample derivatives) taken serially from a subject. In various embodiments, samples are taken every 48 hours, every 24 hours, every 12 hours, or more frequently. Single or multiple GHRsp fragment biomarker measurements within these timeframes are included within the invention. GHRsp fragment biomarker measurements or additional GHRsp fragment biomarker measurements on samples subsequently taken or derived from a subject at any point following an initial sample or assay are also included.

In one embodiment, the biological sample is blood, serum, plasma, saliva, interstitial fluid, urine or tears. In one preferred embodiment, the sample is blood or plasma.

Markers may be measured in samples obtained at the same time, or may be determined from samples obtained at different (e.g., an earlier or later) times. The individual markers may also be measured on the same or different body fluid samples. For example, one GHRsp fragment marker may be measured in a serum or plasma sample and another GHRsp fragment marker may be measured in a urine sample. In addition, assignment of a likelihood may combine an individual GHRsp fragment marker assay result with temporal changes in one or more additional variables.

In one embodiment, the assessment or measuring step comprises detecting binding between the GHRsp fragment biomarker and a binding agent that selectively binds the GHRsp fragment biomarker. The measuring step in one embodiment comprises:

(a) binding the GHRsp fragment biomarker with a binding agent; and (b) measuring the level of bound GHRsp fragment biomarker; and (c) correlating the result to the result to the presence or status of a pneumonia infection, acute decompensated heart failure (ADHF) or the combination of pneumonia and ADHF in the subject.

In another aspect, the GHRsp fragment biomarker binding agent of the invention binds or detects:

(a) GHRsp (1-9) (SEQ ID NO:3);

(b) GHRsp (1-10) (SEQ ID NO:4);

(c) an antigenic variant of any one of (a) or (b).

The binding agent is useful in diagnosing, assessing or monitoring, for example, pneumonia, acute decompensated heart failure (ADHF) or pneumonia and ADHF, which correlates with the release of a GHRsp fragment into the circulation. The binding agent in one embodiment is an anti-GHRsp fragment antibody or an antigen-binding fragment thereof. Most commonly, the antibody is a monoclonal or polyclonal antibody or, if desired, a bispecific, chimeric or humanized antibody. In one embodiment the antibody is a monoclonal antibody.

In one embodiment, the GHRsp fragment biomarker which is bound or detected by the antibody is GHRsp (1-9) (SEQ ID NO:3) or GHRsp (1-10) (SEQ ID NO:4) or both. The antibody may bind the N-terminus or the C-terminus of the GHRsp fragment. The sequences are preferably human sequences.

Specific antigenic peptides which the binding agent selectively binds include human GHRsp (1-9) (SEQ ID NO:3) and/or GHRsp (1-10) (SEQ ID NO:4), or antigenic-binding fragments, or antigenic variants thereof.

In certain embodiments, the assay method is an immunoassay. Antibodies and binding fragments thereof for use in such assays will specifically bind a full length GHRsp fragment marker of interest, and may also bind one or more diagnostic polypeptides that are "related" thereto, as that term is defined hereinafter. Numerous immunoassay formats are known to those of skill in the art. Quantitative, semi-quantitative, or qualitative assays may be used. Preferred assays are quantitative.

The inventions also provide for the use of a ghrelin signal peptide fragment assay for the evaluation of, for example, pneumonia, acuted acute decompensated heart failure (ADHF) or pneumonia and ADHF.

Binding of the GHRsp fragment biomarker in one embodiment is measured using antibodies or antibody fragments that are immobilised on a solid phase.

Levels of the GHRsp fragment biomarker may usefully be measured with an assay selected from RIA, ELISA, fluoroimmunoassay, immunofluorometric assay and immunoradiometric assay.

In another embodiment, levels of a GHRsp fragment biomarker may be measured using mass spectroscopy.

The methods of the invention also comprise measuring the level of one or more non-GHRsp fragment markers of pneumonia, acute decompensated heart failure (ADHF) or pneumonia and ADHF, and comparing the levels against marker levels from a control wherein a deviation in the measured level from the control level of non-GHRsp marker, together with a measured level of GHRsp which deviates from a control or reference level of GHRsp, is diagnostic of pneumonia, or can be used to monitor, for example, pneumonia, ADHF or pneumonia and ADHF.

In another aspect, the invention provides a method for diagnosing, assessing or monitoring pneumonia in a subject using an assay or assays for one or more GHRsp fragment biomarkers in combination with leukocyte counts and/or an assay or assays for one or more of procalcitonin (PCT), Triggering receptor expressed on myeloid cells-1 (TREM-1), C-reactive protein, immunoglobulins, and proinflammatory cytokines. In one embodiment, the GHRsp fragment biomarker is GHRsp (1-9) (SEQ ID NO:3) and/or GHRsp (1-10) (SEQ ID NO:4).

In another aspect, the invention provides a method for diagnosing, assessing or monitoring pneumonia in a subject using an assay for one or more GHRsp fragment biomarkers in combination an assay or assays for one or more of copeptin, cortisol, endotoxin and/or proadrenomedullin. In one embodiment, the GHRsp fragment biomarker is GHRsp (1-9) (SEQ ID NO:3) and/or GHRsp (1-10) (SEQ ID NO:4).

In yet another aspect the present invention provides a method for diagnosing, assessing or monitoring acute decompensated heart failure (ADHF) or pneumonia and ADHF in a subject using an assay or assays for one or more GHRsp fragment biomarkers in combination with leukocyte counts and/or an assay or assays for one or more of procalcitonin (PCT), Triggering receptor expressed on myeloid cells-1 (TREM-1), C-reactive protein, immunoglobulins, proinflammatory cytokines, brain natriuretic protein (BNP), N-terminal proBNP (NT-BNP), blood urea nitrogen, pancreatic stone protein, troponin I and troponin T. In one embodiment, the GHRsp fragment biomarker is GHRsp (1-9) (SEQ ID NO:3) and/or GHRsp (1-10) (SEQ ID NO:4).

The invention is also directed to the use of a GHRsp fragment binding agent in the manufacture of a GHRsp fragment assay for assessing, for example, pneumonia, acute decompensated heart failure (ADHF) or pneumonia and ADHF in a subject, or to the use of a GHRsp fragment biomarker binding agent in the manufacture of a prognostic, assessment, diagnostic or monitoring tool for pneumonia, ADHF or pneumonia and ADHF in a subject, i.e., a tool for pneumonia, ADHF or pneumonia and ADHF diagnosis, prognosis, risk stratification, assessing, staging, monitoring, categorizing and determination of further diagnosis and treatment regimens in subjects with any of the conditions or combinations of conditions referred to above.

In one embodiment the prognostic, assessment, diagnostic, monitoring tool is calibrated to measure GHRsp levels in the range of from at least about 0.1 pmol/L, at least about 1 pmol/L, at least about 5 pmol/L, or at least about 10 pmol/L.

In another aspect, the invention provides a kit for diagnosing, assessing or monitoring pneumonia in a subject, the kit comprising a GHRsp fragment binding agent that binds to GHRsp (1-9) (SEQ ID NO:3) or to GHRsp (1-10) (SEQ ID NO:4) or to both. In one embodiment the kit is calibrated to measure GHRsp fragment levels in the range of from at least about 0.1 pmol/L, at least about 1 pmol/L, at least about 5 pmol/L, or at least about 10 pmol/L. In one embodiment the kit also includes instructions for use in diagnosing, assessing or monitoring subjects with pneumonia or suspected pneumonia, i.e., for use as a tool for one or more or all of pneumonia diagnosis, prognosis, risk stratification, assessing, staging, monitoring, categorizing and determination of further diagnostics and/or treatment regimens in subjects with pneumonia or suspected pneumonia. For example, the instructions may describe methods for diagnosing, assessing, or monitoring pneumonia in a subject, from the GHRsp fragment level measured in a sample or a derivative of a sample and comparing the measured level to a control or reference level. A measured GHRsp fragment biomarker level which deviates from the control or reference level will be indicative of pneumonia. In one embodiment more than one sample is obtained for measurement of GHRsp fragment biomarker levels.

In another aspect, the invention provides a kit for diagnosing, assessing or monitoring acute decompensated heart failure (ADHF) in a subject, the kit comprising a GHRsp fragment binding agent that binds to GHRsp (1-9) (SEQ ID NO:3) or to GHRsp (1-10) (SEQ ID NO:4) or to both. In one embodiment the kit is calibrated to measure GHRsp fragment levels in the range of from at least about 0.1 pmol/L, at least about 1 pmol/L, at least about 5 pmol/L, or at least about 10 pmol/L. In one embodiment the kit also includes instructions for use in diagnosing, assessing or monitoring subjects with ADHF or suspected ADHF, i.e., for use as a tool for one or more or all of ADHF diagnosis, prognosis, risk stratification, assessing, staging, monitoring, categorizing and determination of further diagnostics and/or treatment regimens in subjects with ADHF or suspected ADHF. For example, the instructions may describe methods for diagnosing, assessing, or monitoring ADHF in a subject, from the GHRsp fragment level measured in a sample or a derivative of a sample and comparing the measured level to a control or reference level. A measured GHRsp fragment biomarker level which deviates from the control or reference level will be indicative of ADHF. In one embodiment more than one sample is obtained for measurement of GHRsp fragment biomarker levels.

In yet another aspect, the invention provides a kit for diagnosing, assessing or monitoring pneumonia and acute decompensated heart failure (ADHF) in a subject, the kit comprising a GHRsp fragment binding agent that binds to GHRsp (1-9) (SEQ ID NO:3) or to GHRsp (1-10) (SEQ ID NO:4) or to both. In one embodiment the kit is calibrated to measure GHRsp fragment levels in the range of from at least about 0.1 pmol/L, at least about 1 pmol/L, at least about 5 pmol/L, or at least about 10 pmol/L. In one embodiment the kit also includes instructions for use in diagnosing, assessing or monitoring subjects with pneumonia and ADHF or suspected pneumonia and ADHF, i.e., for use as a tool for one or more or all of pneumonia and ADHF diagnosis, prognosis, risk stratification, assessing, staging, monitoring, categorizing and determination of further diagnostics and/or treatment regimens in subjects with pneumonia and ADHF or suspected pneumonia and ADHF. For example, the instructions may describe methods for diagnosing, assessing, or monitoring pneumonia and ADHF in a subject, from the GHRsp fragment level measured in a sample or a derivative of a sample and comparing the measured level to a control or reference level. A measured GHRsp fragment biomarker level which deviates from the control or reference level will be indicative of pneumonia and ADHF. In one embodiment more than one sample is obtained for measurement of GHRsp fragment biomarker levels.

In various related aspects, the present invention also relates to devices and kits for performing the methods described herein. Suitable kits comprise reagents sufficient for performing an assay for at least one of the described GHRsp fragment markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labelled antibodies, the detectably labelled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labelled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc.) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labelled molecule.

In another aspect the invention provides GHRsp (1-10) (SEQ ID NO:4), a novel peptide discovered and isolated by Applicants. Thus, also provided are isolated and/or purified GHRsp (1-10) (SEQ ID NO:4) peptides (including human GHRsp (1-10) (SEQ ID NO:4) and species variants thereof), GHRsp (1-10) (SEQ ID NO:4) binding agents including anti-GHRsp (1-10) (SEQ ID NO:4) antibodies and antibody binding fragments, assays for GHRsp (1-10) (SEQ ID NO:4) including immunoassays and their use in the detection of GHRsp (1-10) (SEQ ID NO:4) in a biological sample, as described herein. GHRsp (1-10) (SEQ ID NO:4) binding agents and assays are useful in diagnosing, assessing, monitoring, etc., a biological event or disorder which correlates with the release of a GHRsp (1-10) (SEQ ID NO:4) fragment into the circulation. Such events or disorders include pneumonia, acute decompensated heart failure (ADHF) and pneumonia and ADHF, as described herein, and can be used can be used for the diagnosis, prognosis, risk stratification, assessing, staging, monitoring, categorizing and determination of further diagnosis and treatment regimens in subjects with pneumonia or suspected pneumonia, ADHF or suspected ADHF, or pneumonia and ADHF or suspected pneumonia and ADHF.

These and other aspects of the present inventions, which are not limited to or by the information in this Brief Summary of the Invention, are provided below.

BRIEF DESCRIPTION OF FIGURES

FIG. 2 shows a consensus alignment (SEQ ID NO: 11) for ghrelin signal peptide sequences from rat (SEQ ID NO: 5), human (SEQ ID NO: 2), sheep (SEQ ID NO: 6), pig (SEQ ID NO: 7), mouse (SEQ ID NO: 8), dog (SEQ ID NO: 9), and cat (SEQ ID NO: 10), respectively.

FIG. 3 shows a table of cross reactivity data of GHRsp (1-9) (SEQ ID NO:3) biomarker antiserum.

FIG. 4) from a total cohort of 286 human patients sampled.

DETAILED DESCRIPTION

Figure 1:
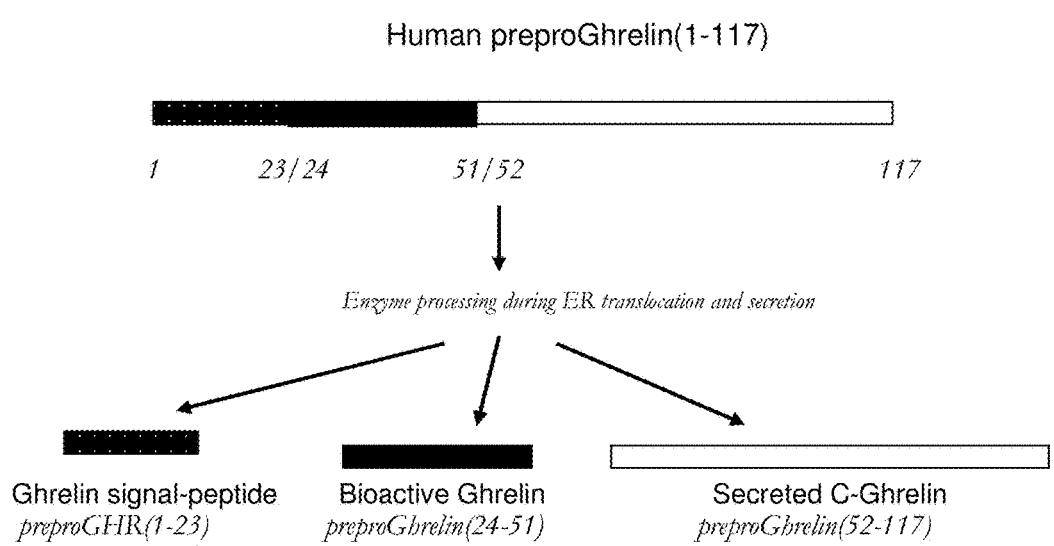
FIG. 1 is a schematic diagram outlining the processing of human preproGhrelin resulting in generation of free signal, N-ghrelin and ghrelin peptides.

Practice of the present inventions may include or employ various conventional techniques of molecular biology (including recombinant and hybridoma techniques), microbiology, cell biology, biochemistry, nucleic acid chemistry, and immunology, which are within the skill of the art. Such techniques are explained fully in the literature, and include but are not limited to, by way of example only, Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"; Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993).

It is to be understood that the inventions are not limited to the particular methodology, protocols, constructs, and reagents described herein and as such may vary. It is also to be understood that the terminology used herein is for the purpose of describing particular embodiments only, and is not intended to limit the scope of the present invention, which will be limited only by the appended claims. As used herein and in the appended claims, the singular forms "a," "an," and "the" include plural reference unless the context clearly indicates otherwise. Thus, for example, reference to a "GHRsp fragment" is a reference to one or more such peptides, and antigenic and species and allelic variants thereof, and includes all equivalents now known or later developed.

Unless defined otherwise, all technical and scientific terms used herein have the same meaning as commonly understood to one of ordinary skill in the art to which the inventions belong. Although any methods, devices, and materials similar or equivalent to those described herein can be used in the practice or testing of the invention, various methods, devices and materials are now described.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

The following terms have the following meanings when used herein.

The term "antibody" refers to an immunoglobulin molecule having a specific structure that interacts (binds) specifically with a molecule comprising the antigen used for synthesizing the antibody or with an antigen closely related to it. As used herein, the term "antibody" broadly includes full length antibodies and binding fragments thereof. Also included are monoclonal and polyclonal antibodies, multivalent and monovalent antibodies, multispecific antibodies (for example bi-specific antibodies), chimeric antibodies, human antibodies, humanized antibodies and antibodies that have been affinity matured. An antibody binds selectively or specifically to an GHRsp polypeptide of the invention if the antibody binds preferentially to the GHRsp, e.g. has less than 25%, or less than 10%, or less than 1% or less than 0.1% cross-reactivity with a non-GHRsp polypeptides. Usually, the antibody will have a binding affinity (dissociation constant (Kd) value), for the antigen or epitope of at least about $10^{-6}$, or $10^{-7}$M, or at least about $10^{-8}$M, or $10^{-9}$M, or $10^{-10}$, or $10^{-11}$ or $10^{-12}$M. Binding affinity may be assessed using surface plasma resonance, for example, or Scatchard analysis.

As used herein, an "antigen-binding fragment" or "antibody fragment" or "binding fragment" when used in reference to an antibody, means a portion of the intact antibody that preferably retains most or all, or minimally at least one of, the normal binding functions of that antibody fragment. Examples of antibody fragments include Fab, Fab', F(ab')$_2$ and Fv fragments, linear antibodies, diabodies, single chain antibodies (ScFV) and multispecific antibodies.

As used herein, the term "antigenic variant" refers to polypeptide sequences different from the specifically identified sequences, wherein 1 to 6 or more or amino acid residues are deleted, substituted, or added. Substitutions, additions or deletions of one, two, three, four, five or six amino acids are specifically contemplated. Variants may be naturally-occurring allelic antigenic variants, or non-naturally occurring antigenic variants. Variants may be from the same or from other species and may encompass homologues, paralogues and orthologues. In certain embodiments, antigenic variants of the polypeptides useful in the invention have biological activities including signal peptide activity or antigenic-binding properties that are the same or similar to those of the parent polypeptides. The term "antigenic variant" with reference to polypeptides encompasses all forms of polypeptides as defined herein. The term "antigenic variant" encompasses naturally occurring, recombinantly and synthetically produced polypeptides. Identity is generally found over a comparison window of at least 5, 6, or 7, at least amino acid positions. For example, for GHRsp (1-9) (SEQ ID NO:3) the comparison window may be over at least 5, 6, 7, or 8 amino acid positions, or over the entire length of the peptide. In the context of GHRsp (1-10) (SEQ ID NO:4) the comparison window may be over at least 5, 6, 7, 8, or 9 amino acid positions, or over the entire length of the peptide.

In one embodiment antigenic variants include peptides who's sequence differs from GHRsp (1-9) (SEQ ID NO:3) or GHRsp (1-10) (SEQ ID NO:4) by one, two, or more conservative amino acid substitutions, deletions, additions or insertions which do not unduly affect the antigenicity of the peptide. Conservative substitutions are known in the art and need not be repeated here. Typically they include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine. Examples of conservative substitutions can also be found in the sequences of GHRsp as shown in the sequence listings whereby the substitutions in different mammalian species compared to the human sequence are shown. Other conservative substitutions can be taken from FIG. 2. Substitutions, deletions, additions or insertions may be made by mutagenesis methods known in the art. A skilled worker will be aware of methods for making phenotypically silent amino acid substitutions. See for example Bowie et al., 1990, Science 247, 1306; Kunkel, T; 1985, PNAS, 85 p 488.

Antigenic variants may be used to prepare binding agents, for example, antibody binding agents, for use in assays of the invention.

The term "binding agent" as used herein refers to any solid or non-solid material capable of binding a GHRsp fragment or an antigenic variant thereof. In one embodiment the term refers to any natural or non-natural molecule that binds to a GHRsp fragment or antigenic variant thereof. Examples of binding agents include proteins, peptides, nucleic acids, carbohydrates, lipids, and small molecule compounds. One selective or specific binding agent is an antibody or antigen-binding fragment thereof.

The GHR signal peptide fragment agents of the invention are typically combined with a carrier, for example a pharmaceutically or veterinarily acceptable carrier or diluent to produce a composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents and/or stabilizing or pH buffering agents may also be present. In addition, adjuvants or other substances that enhance an immune response to an antigen such as a GHRsp, for example, GHRsp (1-10) (SEQ ID NO:4).

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a pneumonia marker, optionally together with other clinical characteristics, to arrive at a diagnosis (that is, the occurrence or nonoccurrence) of pneumonia for the subject from which a sample was obtained or derived and assayed. In the case of the present invention, "diagnosis" also includes using the results of an assay, most preferably an immunoassay, for an acute decompensated heart failure (ADHF) marker or a marker of pneumonia and ADHF, optionally together with other clinical characteristics, to arrive at a diagnosis (that is, the occurrence or nonoccurrence) of ADHF or pneumonia and ADHF for the subject from which a sample was obtained or derived and assayed That such a diagnosis is "determined" is not meant to imply that the diagnosis is 100% confirmed. The skilled clinician will not use biomarker results in an informational vacuum, but rather test results together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold. Similarly, a prognostic risk signals a probability ("a likelihood") that a given course or outcome will occur. A level or a change in level of a prognostic indicator, which in turn is associated with an increased probability of morbidity (e.g., worsening lung function, including bloody effusions, diffuse alveolar damage and haemorrhage, etc.) is referred to as being "indicative of an increased likelihood" of an adverse outcome in a patient.

The term "epitope" includes any antigenic (e.g., a protein) determinant capable of specific binding to an antibody and/or a T cell receptor. That is, a site on an antigen to which B and/or T cells respond. Epitopic determinants usually consist of chemically active surface groupings of molecules such as amino acids or sugar side chains, and usually have specific three dimensional structural characteristics, as well as specific charge characteristics. An epitope typically includes at least 3, 5 or 8-10 amino acids. The amino acids may be contiguous, or non-contiguous amino acids juxtaposed by tertiary folding. Conformational and nonconformational epitopes are distinguished in that the binding to the former but not the latter is lost in the presence of denaturing solvents.

A "fragment" of a polypeptide is a subsequence of the polypeptide that performs a function that is required for specific antibody binding and/or provides three dimensional structure of the polypeptide. The term may refer to a polypeptide, an aggregate of a polypeptide such as a dimer or other multimer, a fusion polypeptide, a polypeptide fragment, a polypeptide antigenic variant, or derivative thereof. In one embodiment the fragment retains the antigenic-binding properties of GHRsp (1-9) (SEQ ID NO:3), GHRsp (1-10) (SEQ ID NO:4), or other polypeptide of the invention or polypeptide described herein.

"GHRsp" refers to the complete 23 amino acid GHR signal peptide for the human preproghrelin sequence (SEQ ID NO:1). Also referred to as "GHRsp (1-23)," it is shown separately in SEQ ID NO:2. GHRsp fragment biomarkers include GHRsp-derived or GHRsp-related polypeptides, comprising, consisting essentially of, or consisting of an antigenic variant or fragment of GHRsp. Fragments useful as GHRsp fragment biomarkers include GHRsp (1-9) (SEQ ID NO:3), i.e., the first nine amino acids of GHRsp (1-23) and GHRsp (1-10) (SEQ ID NO:4), i.e., the first ten amino acids of GHRsp (1-23). In one embodiment GHRsp (1-23) (SEQ ID NO:2) and GHRsp (1-10) (SEQ ID NO:4) function as antigenic polypeptides to which an antibody can bind. Variants and fragments of GHRsp (1-23) (SEQ ID NO:2) and GHRsp (1-10) (SEQ ID NO:4) include antigenic variants and fragments which retain at least their antigenic-binding functions.

The term "isolated" as applied to the polypeptide sequences disclosed herein is used to refer to sequences that are removed from their natural cellular environment. An isolated molecule may be obtained by any method or combination of methods including biochemical, recombinant, and synthetic techniques. The polypeptide sequences may be prepared by at least one purification step.

A level "higher" or "lower" than a control or reference value, or a change, difference or deviation from a control or reference value, in one embodiment is statistically significant. In a another, higher levels, lower levels, deviation, and changes can be determined by recourse to assay reference limits or reference intervals.

An "isolated antibody" is an identified antibody which has been separated or recovered, or both, from a component of its natural environment. For example, separated from proteins including enzymes and hormones. In one embodiment, the antibody is purified to at least 95%, or 96% or 97% or 98% or 99% by weight of antibody. Purity can be determined by the Lowry method, for example. Ordinarily the antibody will be prepared by at least one purification step.

The term "mass spectrometry" as used herein refers to methods of filtering, detecting, and measuring ions based on their mass to charge ratio. See for example U.S. Pat. No. 5,719,060, U.S. Pat. No. 6,204,500, U.S. Pat. No. 6,107,623, U.S. Pat. No. 6,124,137, U.S. Pat. No. 6,225,047, U.S. Pat. No. 6,268,144, U.S. Pat. No. 7,057,165, and U.S. Pat. No. 7,045,366. Common mass spectrometry techniques include matrix-assisted laser desorption ionization (MALDI) and surface-enhanced laser desorption ionization (SELDI). Both may be coupled with time of flight analysers (MALDI-TOF and SELDI-TOF) which allow for analysis of analytes at femtomole levels in very short ion pulses. Versions of SELDI discussed for example in U.S. Pat. No. 5,719,600, U.S. Pat. No. 6,124,137, and U.S. Pat. No. 6,225,047 which are useful in this invention also include Surface-Enhanced Affinity Capture (SEAC), Surface-Enhanced Neat Desorption (SEND), and Surface-Enhanced Photolabile Attachment and Release (SEPAR).

As used herein, a "monoclonal antibody" means an antibody that is a highly specific antibody directed against a single target antigen. A monoclonal antibody may be obtained from a population of homogenous or substantially homogenous antibodies wherein each monoclonal antibody is identical and/or bind the same epitope, except for natural mutations which may occur in minor amounts. Monoclonal antibodies are prepared using methods known the art.

The term "purified" as used herein does not require absolute purity. Purified refers in one embodiment to at least 90%, or 95%, or 98%, or 99% homogeneity of, to provide an example, a polypeptide or antibody in a sample.

As used herein, the term "relating a signal to the presence or amount" of an analyte reflects that assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of about 4-8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the GHRsp markers described herein refers to one or more antigenic variants that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

Preferably, an analyte is measured in a sample. The term "sample" or "biological sample" as used herein means any sample taken or derived from a subject. Such a sample may be obtained from a subject, or may be obtained from biological materials intended to be provided to the subject. For example, a sample may be obtained from blood being evaluated for possible transfusion into a subject, and an analyte measurement used to evaluate the blood for preexisting pneumonia infection. Included are samples taken or derived from any subjects such as from normal healthy subjects and/or healthy subjects with no clinical history of pneumonia. Preferred samples are body fluid samples. The term "body fluid sample" as used herein refers to a sample of bodily fluid obtained for the purpose of, for example, diagnosis, prognosis, classification or evaluation of a subject of interest, such as a patient. In certain embodiments, such a sample may be obtained for the purpose of determining the outcome of an on-going pneumonia infection or the effect of a treatment regimen for pneumonia. The sample may be any sample known in the art in which a GHRsp fragment can be detected. Included are any body fluids such as blood, plasma, serum, cerebrospinal fluid, saliva, sputum, urine, pleural effusions, interstitial fluid, synovial fluid, lymph, tears, as well as tissues, for example. In addition, one of skill in the art would realize that certain body fluid samples would be more readily analyzed following a fractionation or purification procedure, for example, separation of whole blood into serum or plasma components.

The term "subject" as used herein refers to a human or non-human organism. "Subject" as used herein is preferably a mammal and includes human, and non-human mammals such as cats, dogs, horses, cows, sheep, deer, mice, rats, primates (including gorillas, rhesus monkeys and chimpanzees), possums and other domestic farm or zoo animals. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans who may receive or are receiving medical care for a disease or condition. This includes persons with no defined illness who are being investigated for signs of pathology.

The term "treat", "treating" or "treatment" and "preventing" refer to therapeutic or prophylactic measures undertaken to alleviate, ameliorate, manage, prevent, restrain, stop or reverse progression of a pneumonia infection characterized by a GHRsp fragment level which shows a deviation from normal control levels.

A biomarker can be understood to be any biomolecule that is associated with a particular pathological or physiological state. Ideally, a pneumonia biomarker, a biomarker for acute decompensated heart failure (ADHF) or a biomarker for pneumonia and ADHF should be one which cannot be detected or whose value is very low in the absence of inflammation; it should rise with increasing inflammatory processes and should decrease with resolving inflammation. There is a growing need for biomarkers to evaluate their use in the diagnosis of pneumonia, ADHF or patients with both pneumonia and ADHF. See Schuetz P, Christ-Crain M, Mueller B. Procalcitonin and other biomarkers to improve assessment and antibiotic stewardship in infections—hope or hype? Swiss Medical Weekly. 2009; 139(23-24):318-326. Applicants' inventions meet these needs.

A person skilled in the art will appreciate the terms "biomarker" and "marker" in the context of the present invention are used interchangeably and are intended to mean the same thing.

Ghrelin (GHR) is a polypeptide hormone produced by the endocrine cells in the placenta, kidney, hypothalamus and pituitary. In the stomach (the main site of ghrelin production), epithelial cells lining the fundus produce ghrelin. Ghrelin is involved in the regulation of energy balance. Ghrelin acts to increase appetite, food consumption and ultimately body weight in an individual by activating hypothalamic feeding centers. Hyperglycemia is induced, and insulin release inhibited by ghrelin. Ghrelin and its receptor are also found in cardiovascular tissue (Garcia, E et al.; Ghrelin and Cardiovascular health, Current Opinion in Pharmacology, vol 6, Issue 2, 2006, p. 142-147). As shown in SEQ ID NO:1, preproGHR is a 117 amino acid molecule (see Table 1, below). It consists of two polypeptide chains (A and B), linked by disulsphide bridges. Preproghrelin (1-117) (SEQ ID NO:1) is cleaved to give a signal peptide of 23 amino acids (SEQ ID NO:2; see Table 2, below), proghrelin of 94 amino acids, and the ghrelin hormone of 28 amino acids. Processing of human preproghrelin is shown in FIG. 1.

TABLE 1

Ghrelin Sequences

| | | | | |
|---|---|---|---|---|
| SEQ ID NO: 1 | Human Preproghrelin | MPSPGTVCSL DGGQAEGAED YQQHSQALGK | LLLGMLWLDL EHQRVQQRKE ELEVRFNAPF FLQDILWEEA | AMAGSSFLSP SKKPPAKLQP DVGIKLSGVQ KEAPADK RALAGWLRPE |
| SEQ ID NO: 2 | Human Ghrelin Signal Sequence 1-23 | MPSPGTVCSL | LLLGMLWLDL | AMA |
| SEQ ID NO: 3 | GHRsp (1-9) | MPSPGTVCS | | |
| SEQ ID NO: 4 | GHRsp (1-10) | MPSPGTVCSL | | |

Confounding customary views, Applicants have discovered that GHRsp fragments appear in the circulation in pneumonia, and that GHRsp fragments are useful as a circulating biomarker for pneumonia. For example, in subjects with pneumonia the level of GHRsp will be above the normal control or reference level.

Applicants have also surprisingly discovered that GHRsp fragments appear in the circulation of subjects with acute decompensated heart failure (ADHF) as well as in the circulation of subjects with pneumonia and ADHF. For example, the level of GHRsp will be above the normal control of reference level in these subjects.

The present inventions relate to methods and compositions and kits for diagnosis, differential diagnosis, risk stratification, monitoring, classifying and determination of treatment regimens in subjects with pneumonia or suspected pneumonia through measurement of one or more GHRsp fragment markers. The present invention also relates to methods and compositions and kits for diagnosis, differential diagnosis, risk stratification, monitoring, classifying and determination of treatment regimens in subjects with acute decompensated heart failure (ADHF) or suspected ADHF through measurement of one or more GHRsp fragment markers. The present invention further relates to methods and compositions and kits for diagnosis, differential diagnosis, risk stratification, monitoring, classifying and determination of treatment regimens in subjects with pneumonia and ADHF or suspected pneumonia and ADHF through measurement of one or more GHRsp fragment markers. In various embodiments, a measured concentration of one or more markers selected from the group consisting of GHRsp (1-9) (SEQ ID NO:3) or GHRsp (1-10) (SEQ ID NO:4) (see Table, 1, above), for example, or one or more markers related thereto, are correlated to the status of the subject. In various embodiments, the assay used to determine the amount, concentration or presence of a GHRsp fragment marker provides a quantitative result (e.g., a measurement in pmol/L), a semi-quantitative result (e.g., a concentration within a range or concentrations) or a qualitative result (e.g., "Yes-No" for infection). Quantitative, semi-quantitative, and qualitative assays are well-known in the art and need not be described here.

The invention provides a method for predicting, diagnosing or monitoring pneumonia in, and/or determining further diagnostics to be carried out on and/or treatment for, a subject, the method comprising:
  (a) measuring the level of a GHRsp fragment in a biological sample from the subject; and
  (b) comparing the level of GHRsp fragment with the GHRsp fragment level from a control or reference level,
wherein a deviation in the measured level from the control or reference level is indicative of pneumonia. In addition, the results of the GHRsp fragment marker methods of the invention and comparisons with the GHRsp fragment level from a control or reference level, allow for risk stratification, monitoring, classifying and determination of treatment regimens in subjects with pneumonia or suspected pneumonia.

The invention also provides a method for predicting, diagnosing or monitoring acute decompensated heart failure (ADHF) in, and/or determining further diagnostics to be carried out on and/or treatment for, a subject, the method comprising:
  (a) measuring the level of a GHRsp fragment in a biological sample from the subject; and
  (b) comparing the level of GHRsp fragment with the GHRsp fragment level from a control or reference level,
wherein a deviation in the measured level from the control or reference level is indicative of ADHF. In addition, the results of the GHRsp fragment marker methods of the invention and comparisons with the GHRsp fragment level from a control or reference level, allow for risk stratification, monitoring, classifying and determination of treatment regimens in subjects with ADHF or suspected ADHF.

The present invention further provides a method for predicting, diagnosing or monitoring pneumonia and acute decompensated heart failure (ADHF) in, and/or determining further diagnostics to be carried out on and/or treatment for, a subject, the method comprising:
(a) measuring the level of a GHRsp fragment in a biological sample from the subject; and
(b) comparing the level of GHRsp fragment with the GHRsp fragment level from a control or reference level, wherein a deviation in the measured level from the control or reference level is indicative of pneumonia and ADHF. In addition, the results of the GHRsp fragment marker methods of the invention and comparisons with the GHRsp fragment level from a control or reference level, allow for risk stratification, monitoring, classifying and determination of treatment regimens in subjects with pneumonia and ADHF or suspected pneumonia and ADHF.

The GHRsp fragments may be measured using quantitative, semi-quantitative or qualitative assay methods.

Commonly, as mentioned herein, the deviation will be a higher measured level of GHRsp fragment compared to a control level, although this is not necessary.

Examples of specific antigenic peptide fragments are GHRsp 1-9 (SEQ ID NO:3) and GHRsp (1-10) (SEQ ID NO:4).

Specific polypeptides of the invention include a polypeptide having the amino acid sequence of SEQ ID NO:3 and SEQ ID NO:4 as set forth in the accompanying sequence listing. Also contemplated are antigenic variants and fragments of these polypeptides as defined herein, or amino acid sequences having at least 70%, 75%, 80%, 85%, 90%, 95% or 99% amino acid identity to the polypeptide of SEQ ID NO:3 or 4. In one embodiment the antigenic variants or fragments are functionally equivalent antigenic variants or fragments. That is the antigenic variants or fragments maintain the functions of SEQ ID NO:3 or 4 as antigens. The polypeptides may be used in the preparation of anti-GHRsp fragment antibodies.

In addition to computer/database methods known in the art, polypeptide antigenic variants may be identified by physical methods known in the art, for example, by screening expression libraries using antibodies raised against polypeptides of the invention (Sambrook et al., Molecular Cloning: A Laboratory Manual, 2nd Ed. Cold Spring Harbor Press, 1987) by recombinant DNA techniques also described by Sambrook et al. or by identifying polypeptides from natural sources with the aid of such antibodies.

Polypeptides, including antigenic variant polypeptides, may be prepared using peptide synthesis methods well known in the art, such as direct peptide synthesis using solid phase techniques (e.g. Merrifield, 1963, in J. Am Chem. Soc. 85, 2149; Stewart et al., 1969, in Solid-Phase Peptide Synthesis, WH Freeman Co, San Francisco Calif.; Matteucci et al. J. Am. Chem. Soc. 103:3185-3191, 1981, and Atherton et al., in Solid Phase Peptide Synthesis: a practical approach, IRL press (1989)) or automated synthesis, for example using a Synthesiser from Applied Biosystems (California, USA). Mutated forms of the polypeptides may also be produced using synthetic methods such as site-specific mutagensis of the DNA encoding the amino acid sequence as described by Adelmen et al; DNA 2, 183 (1983). See also Protein Protocols Handbook; Walker, 3. Humana Press 2002.

The polypeptide fragments and antigenic variant polypeptide may be isolated for the use in the preparation of binding agents including, for example, antibody binding agents. They may be isolated or purified from natural sources using a variety of techniques that are well known in the art, including, e.g., HPLC, ion-exchange chromatography, and immunochromatography (e.g., Deutscher, 1990, Ed, Methods in Enzymology, Vol. 182, *Guide to Protein Purification*, and Protein Protocols Handbook). As noted above, the polypeptides and antigenic variants have utility in generating antibodies, and generating ligands amongst other uses.

Broadly the invention provides for the preparation and use of a ghrelin signal peptide fragment assay for the evaluation of pneumonia, and related kits and manufactures, which may include or be associated with instructions for use.

In another aspect, the present invention provides a method for evaluating pneumonia infection in a subject, comprising performing an assay method configured to detect a ghrelin signal peptide fragment in a body fluid sample obtained from the subject to provide an assay result; and correlating the assay result to the presence or status of a pneumonia infection in the subject. In one embodiment the correlation step comprises correlating the assay result to one or more of risk stratification, staging, classifying and monitoring of the existence or status of a pneumonia infection the subject. In another embodiment, the correlating step comprises assigning a treatment regimen to the subject based on the assay result. In another embodiment, the correlating step comprises assessing a clinical outcome following a treatment regimen for a pneumonia infection in a subject.

In a further aspect, the present invention provides a method for evaluating acute decompensated heart failure (ADHF) in a subject, comprising performing an assay method configured to detect a ghrelin signal peptide fragment in a body fluid sample obtained from the subject to provide an assay result; and correlating the assay result to the presence or status of ADHF in the subject. In one embodiment the correlation step comprises correlating the assay result to one or more of risk stratification, staging, classifying and monitoring of the existence or status of ADHF the subject. In another embodiment, the correlating step comprises assigning a treatment regimen to the subject based on the assay result. In another embodiment, the correlating step comprises assessing a clinical outcome following a treatment regimen for ADHF in a subject.

In yet a further aspect, the present invention provides a method for evaluating pneumonia and acute decompensated heart failure (ADHF) in a subject, comprising performing an assay method configured to detect a ghrelin signal peptide fragment in a body fluid sample obtained from the subject to provide an assay result; and correlating the assay result to the presence or status of pneumonia and ADHF in the subject. In one embodiment the correlation step comprises correlating the assay result to one or more of risk stratification, staging, classifying and monitoring of the existence or status of pneumonia and ADHF the subject. In another embodiment, the correlating step comprises assigning a treatment regimen to the subject based on the assay result. In another embodiment, the correlating step comprises assessing a clinical outcome following a treatment regimen for pneumonia and ADHF in a subject.

In still another embodiment, the assay result is a measured concentration of a ghrelin signal peptide fragment, and the correlation step comprises comparing the concentration to a threshold concentration. In one embodiment, the threshold is a concentration of the ghrelin signal peptide fragment obtained from the subject at an earlier time point. In other embodiments, the threshold is a concentration of the ghrelin signal peptide fragment obtained from a normal subject population and/or a concentration of the ghrelin signal peptide fragment obtained from a subject population. In yet another embodiment, the threshold is a concentration of the ghrelin signal peptide fragment selected to distinguish from a population of subjects a first subpopulation having, for example, pneumonia, acute decompensated heart failure (ADHF) or pneumonia and ADHF relative to a second subpopulation not having these conditions or combination of conditions.

In still another embodiment, the subject is selected for evaluation of pneumonia based on one or more symptoms of pneumonia, including cough with sputum production, fever, pleural effusion, sharp chest pain on inspiration, and breathlessness.

In yet another embodiment, the subject is selected for evaluation of acute decompensated heart failure (ADHF) based on one or more symptoms of ADHF, including breathlessness (dyspnea), edema and fatigue.

In yet a further another embodiment, the subject is selected for evaluation of pneumonia and ADHF based on one or more symptoms of pneumonia, including cough with sputum production, fever, pleural effusion, sharp chest pain on inspiration, and breathlessness and/or one or more symptoms of ADHF, including breathlessness (dyspnea), edema and fatigue.

In still another embodiment, the correlating step comprises assessing whether or not pneumonia, ADHF or pneumonia and ADHF is improving or worsening in a subject based on the assay result.

In another aspect the invention provides a method for monitoring a subject's response to treatment for pneumonia, the method comprising measuring the level of a GHRsp rafgment biomarker for pneumonia in a biological sample from the subject and comparing the level of said GHRsp fragment with the GHRsp fragment level from a control, reference, or reference range wherein a change in the measured level of GHRsp fragment biomarker from the control or reference level is indicative of a response to the treatment.

In a further aspect the invention provides a method for monitoring a subject's response to treatment for acute decompensated heart failure (ADHF), the method comprising measuring the level of a GHRsp rafgment biomarker for ADHF in a biological sample from the subject and comparing the level of said GHRsp fragment with the GHRsp fragment level from a control, reference, or reference range wherein a change in the measured level of GHRsp fragment biomarker from the control or reference level is indicative of a response to the treatment.

In another aspect the invention provides a method for monitoring a subject's response to treatment for pneumonia and acute decompensated heart failure (ADHF), the method comprising measuring the level of a GHRsp rafgment biomarker for pneumonia and ADHF in a biological sample from the subject and comparing the level of said GHRsp fragment with the GHRsp fragment level from a control, reference, or reference range wherein a change in the measured level of GHRsp fragment biomarker from the control or reference level is indicative of a response to the treatment.

The skilled reader will appreciate that for evaluation purposes, the GHRsp fragment biomarker level will generally correlate with a reference value or range or a control value.

As used herein a control can be an individual or group from which GHRsp fragment biomarker samples are taken and a mean GHRsp fragment biomarker level determined. Usually, the individual or group will comprise normal healthy individuals or a group of individuals not known to be suffering from pneumonia or condition such as acute decompensated heart failure (ADHF) or both. Data from the Examples show that GHRsp fragment biomarker levels in most individuals are less than 12 pmol/L, and the median control level was about 11.1 pmol/L. These data also show that GHRsp fragment biomarker levels in individuals with pneumonia are greater than 17 pmol/L, and the median level was about 17.8 pmol/L. Alternatively, the control level may be assessed based on a plurality of readings from previously tested individuals or groups. Alternatively, the control may be one or more readings or the mean of such readings taken from the same subject at an earlier time.

Data from the Examples also show that GHRsp fragment biomarker levels in individuals with acute decompensated heart failure (ADHF) are greater than 16 pmol/L, and the median level was about 16.1 pmol/L, whereas GHRsp fragment biomarker levels in individuals with pneumonia and acute decompensated heart failure (ADHF) are greater than 19 pmol/L, and the median level was about 19.75 pmol/L. Relative to control levels, these data demonstrate the clinical usefulness in using GHRsp fragments as a biomarker of pneumonia and ADHF, as well as ADHF.

It will be appreciated that the step of measuring GHRsp fragment biomarker levels in a sample may be a single measurement on a single sample, or repeated measurements on a number of samples depending on the patient being evaluated. Measurement may comprise, for example, 1 to 20 measurements of a GHRsp fragment biomarker, 1 to 10, 1 to 5, 1 to 3, 1 or 2, or 2 or 3 measurements, in samples taken or derived from a subject at different times. In one embodiment the measurements are on samples taken before and after treatment for pneumonia, acute decompensated heart failure (ADHF) or patients who present with both pneumonia and ADHF. Single, or repeated measurements may also be taken to establish whether the GHRsp fragment biomarker level risen or has fallen compared to the normal control level, or related reference levels or ranges, or a previously measured level for the patient.

In one embodiment, the method comprises measuring GHRsp fragment biomarker levels in at least one sample taken within about the first hour of presentation, followed by measuring GHRsp fragment biomarker levels in 1 or 2 samples taken within about four to eight hours, or about six to twelve hours, or about twelve to twenty-four hours or more of presentation, or initial measurement of the GHRsp fragment level.

The biological sample as defined above can be any biological material in which a GHRsp fragment biomarker can be located or secreted. In one embodiment a biological sample is a circulatory biological sample, for example blood, serum or plasma.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample (quantitatively, semi-quantitatively or qualitatively). Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labelled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labelled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups).

Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described biomarkers for pneumonia, acute decompensated heart failure (ADHF) or pneumonia and ADHF. The kit comprises reagents for the analysis of at least one test sample which comprises at least one antibody against the marker. The kit can also include devices and instructions for performing one or more of the diagnostic and/or prognostic correlations described herein. Preferred kits will comprise an antibody pair for performing a sandwich assay, or a labelled species for performing a competitive assay, for the analyte. Preferably, an antibody pair comprises a first antibody conjugated to a solid phase and a second antibody conjugated to a detectable label, wherein each of the first and second antibodies that bind a pneumonia marker. Most preferably each of the antibodies are monoclonal antibodies. The instructions for use of the kit and performing the correlations can be in the form of labelling, which refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

Antibodies

As noted above, antibody or antibodies as used herein refers to a peptide or polypeptide derived from, modelled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; 3. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

For a further discussion of antibodies and fragments see for example PNAS USA 81: 6851-6855 (1984), Protein Eng 8(10) 1057-1062 (1995); The Pharmacology of Monoclonal Antibodies, vol. 113, Springer-verlag 1994, Rosenburg and Moore Eds; PNAS USA 90: 6444-6448 (1993); Nature 321: 522-525 (1986); Nature 332: 323-329 (1988), and WO 2005/003154.

Also included is antiserum obtained by immunizing an animal such as a mouse, rat or rabbit with GHRsp fragment or antigenic variant thereof. The antibodies may bind to a common GHRsp fragment sequence in a group of GHRsp fragments, or to a specific GHRsp fragment, or even to sets of GHRsp fragments. In brief, methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include GHRsp or a fragment or antigenic variant thereof or a fusion protein thereof. It may be useful to conjugate the immunizing agent to a protein known to be immunogenic in the mammal being immunized. Examples of such immunogenic proteins include but are not limited to keyhole limpet hemocyanin, bovine serum albumin, bovine thyroglobulin, and soybean trypsin inhibitor. Examples of adjuvants which may be employed include Freund's complete adjuvant and MPL TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods well known in the art. See for example Kohler and Milstein, 1975 (Kohler Continuous Cultures of Fused Cells Secreting Antibody of Predefined Specficity. Nature, (5517) 256, 495-497), U.S. Pat. No. 4,196,265, U.S. Pat. No. 4,816,567 and Golemis (supra). The hybridoma cells may be cultured in a suitable culture medium, alternatively, the hybridoma cells may be grown in vivo as ascites in a mammal. Preferred immortalized cell lines are murine myeloma lines, which can be obtained, for example, from the American Type Culture Collection, Virginia, USA. Immunoassays may be used to screen for immortalized cell lines which secrete the antibody of interest. Sequences of GHRsp or fragments or antigenic variants thereof may be used in screening.

Well known means for establishing binding specificity of monoclonal antibodies produced by the hybridoma cells include immunoprecipitation, radiolinked immunoassay (RIA), enzyme-linked immunoabsorbent assay (ELISA) and Western blot. (Lutz et al., Exp. Cell. Res. 175:109-124 (1988), Golemis (supra), and Howard (supra)). For example, as noted above, the binding affinity of the monoclonal antibody can, for example, be determined by the Scatchard analysis described in Munson et al., Anal Biochem 107: 220 (1980). Samples from immunised animals may similarly be screened for the presence of polyclonal antibodies.

Monoclonal antibodies can also be obtained from recombinant host cells. DNA encoding the antibody can be obtained from a hybridoma cell line. The DNA is then placed into an expression vector, transfected into host cells (e.g., COS cells, CHO cells, E. coli cells) and the antibody produced in the host cells. The antibody may then be isolated and/or purified using standard techniques.

The monoclonal antibodies or fragments may also be produced by recombinant DNA means (see for example U.S. Pat. No. 4,816,567). DNA modifications such as substituting the coding sequence for human heavy and light chain constant domains in place of the homologous murine sequences (U.S. Pat. No. 4,816,567 above) are also possible. The antibodies may be monovalent antibodies. Methods for preparing monovalent antibodies are well known in the art (U.S. Pat. Nos. 5,334,708, 5,821,047, and 7,476,724). Production of chimeric (U.S. Pat. No. 4,816,567), bivalent antibodies (U.S. Pat. No. 5,843,708) and multivalent antibodies are also contemplated herein (U.S. Pat. No. 6,020,153).

Other known art techniques for monoclonal antibody production such as from phage libraries, may also be used. See for example, Nature 352: 624-628 (1991).

The monoclonal antibodies secreted by the cells may be isolated or purified from the culture medium or ascites fluid by conventional immunoglobulin purification procedures such as, for example, reverse phase HPLC, protein A-Sepharose, hydroxyapatite chromatography, gel electrophoresis, dialysis, or affinity chromatography. See for example, Scopes, Protein Purification: Principles and Practice, Springer-Verlag, NY (1982).

Bispecific antibodies may also be useful. These antibodies are monoclonal, preferably human or humanized, antibodies that have binding specificities for at least two different antigens. For example GHRsp or a antigenic variant or fragment thereof, and an antigen selected from the group including preproghrelin, ANP, ANP-SP, CK-MB, TnT, TnI, BNP, BNP-SP, NT-BNP, myoglobin, LDH, aspartate aminotransferase, H-FABP, ischemia modified albumin, endothelin, adrenomedullin, rennin and angiotensin II. Antibodies with greater than two specificities for example trispecific antibodies are also contemplated herein.

Methods for making bispecific antibodies are known in the art. See for example Milstein and Cuello 1983[19], Suresh et al., 1986[20] and Brennan et al., 1985.[21]

Antibodies used in the immunoassays described herein preferably specifically bind to a pneumonia marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, antibodies bind with affinities of at least about $^{-6}$, or $10^{-7}M$, or at least about $10^{-8}M$, or $10^{-8}M$, or $10^{-10}$, or $10^{41}$ or $10^{-12}M$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., J. Immunoassay 12: 425-43, 1991; Nelson and Griswold, Comput. Methods Programs Biomed. 27: 65-8, 1988.

Numerous publications discuss the use of phage display technology to produce and screen libraries of polypeptides for binding to a selected analyte. See, e.g., Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labelled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from pneumonia, acute decompensated heart failure (ADHF) or pneumonia and ADHF, or in persons known to be free of pneumonia, ADHF or pneumonia and ADHF. Often, this takes the form of comparing an assay result in the form of a biomarker concentration to a predetermined threshold selected to be indicative of the occurrence or nonoccurrence of pneumonia or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

As described in the below Examples with regard to pneumonia and/or acute decompensated heart failure and GHRsp fragments, population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., Intensive Care Med. 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, with a corresponding sensitivity greater than 0.2, 0.3 or 0.4, still more preferably at least 0.5, 0.6, 0.7, 0.8, 0.9, and most preferably greater than 0.95; a sensitivity of greater than 0.5, preferably at least 0.6, 0.7, or 0.8, even more preferably at least 0.9 and most preferably at least 0.95, with a corresponding specificity greater than 0.2, 0.3 or 0.4, still more preferably at least 0.5, 0.6, 0.7, 0.8 or 0.9, and most preferably greater than 0.95; at least 75% sensitivity, combined with at least 75% specificity; a ROC curve area of greater than 0.5, preferably at least 0.6, more preferably 0.7; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1.

An exemplar ROC curve demonstrating the usefulness of GHRsp fragment measurement to detect pneumonia is shown in the below Examples. Initially, blood samples were drawn from 123 consecutive patients (whose primary complaint was breathlessness/dyspnea) at their time of presentation to the Emergency Department of Christchurch Hospital, New Zealand. 23 out of 123 patients (18.6%) were determined to have pneumonia by independent gold diagnostic criteria including clinical workup, chest x-ray and laboratory analysis of sputum for pneumococcal bacteria. Median GHRsp fragment for pneumonia patients was 11.1 pmol/L, whereas median for those without pneumonia was 8.8 pmol/L. Prepared plasma samples were then analyzed by the described GHRsp fragment RIA. Subsequent analysis of these presentation values reveals that GHRsp is able to detect pneumonia, with an accompanying ROC area under the curve (AUC) of 0.714 (p<0.01). From the ROC curve, the results also show 83% specificity/48% sensitivity at 11.1 pmol/L, and 92% specificity/35% sensitivity at 13.1 pmol/L. These data confirm the suitability of the GHRsp fragment assay for meaningful decision making and represent a good level of clinical usefulness.

Additional clinical indicia may be combined with the pneumonia marker assay result(s) of the present invention. These include chest X-ray, lab analysis of sputum for pneumococcal infection, etc., as well as measurement of C-reactive protein, leukocyte count, immunoglobulins, proinflammatory cytokines, procalcitonin (PCT) and Triggering receptor expressed on myeloid cells-1 (TREM-1).

Combining assay results/clinical indicia in this manner can comprise the use of multivariate logistical regression, loglinear modeling, neural network analysis, n-of-m analysis, decision tree analysis, etc. This list is not meant to be limiting.

One skilled in the art readily appreciates that the present invention is well adapted to carry out the objects and obtain the ends and advantages mentioned, as well as those inherent therein. The further descriptions and examples provided herein are representative of certain embodiments, are exemplary, and are not intended as limitations on the scope of the invention.

Peptide Assays

In one embodiment the measuring step comprises detecting binding between a GHRsp fragment biomarker and a binding agent that binds, (including selectively or specifically binds) GHRsp or a fragment or antigenic variant thereof. As a pre-step in the measurement a GHRsp fragment biomarker polypeptide may be bound with a binding agent that binds GHRsp or a fragment or antigenic variant thereof.

Accordingly, in one embodiment the invention provides an assay for a GHRsp fragment biomarker in a biological sample, the assay comprising detecting and measuring the level of GHRsp fragment biomarker in the sample using any known methods.

In one embodiment, the invention provides an assay for a GHRsp fragment biomarker comprising:
  (a) binding one or more GHRsp fragment biomarker polypeptides from a biological sample; and
  (b) measuring the level of bound GHRsp fragment biomarker polypeptide.

In one embodiment, the GHRsp fragment biomarker polypeptide is GHRsp (1-9) (SEQ ID NO:3) or a antigenic variant or fragment thereof. It will be appreciated that in one embodiment more than one type of GHRsp polypeptide may be bound in the assay, for example, GHRsp (1-9) (SEQ ID NO:3) and GHRsp (1-10) (SEQ ID NO:4).

In one embodiment, the GHRsp fragment biomarker polypeptide is bound using a binding agent. The binding agent may be a selective (specific) binding agent. That is, it has low cross-reactivity with other markers of biological events, and more particularly ghrelin. The binding agent in one embodiment is an antibody or antigen-binding fragment thereof. Where an antibody is used in the assay, the antibody may be raised against any antigenic part of the GHRsp fragment biomarker, including the N-terminal, or C-terminal. In one embodiment the antibody is raised against GHRsp (1-9) (SEQ ID NO:3) or an antigenic variant or fragment thereof.

The present invention also relates to such binding agents, antibodies, and antigen-binding fragments of the antibodies and their uses in an assay, or in the manufacture of an assay, prognostic, diagnostic or monitoring tool for GHRsp fragments. The assay or tool may be used to monitor pneumonia in a subject, or it may be used to monitor acute decompensated heart failure (ADHF) in a subject, or it may be used to monitor a subject who has both pneumonia and ADHF.

In one embodiment, the antibody binds the N-terminus (1-9) of GHRsp. An example of a specific antigenic peptides which the binding agent selectively binds includes GHRsp (1-9) (SEQ ID NO:3).

Binding of a GHRsp fragment biomarker can be detected by any means known in the art including specific (antibody based) and non specific (such as HPLC solid phase). Most commonly, antibodies herein are detected using an assay such as ELISA or RIA as noted above. Competitive binding assays, sandwich assays, non-competitive assays, fluoroimmunoassay, immunofluorometric assay, or immunoradiometric assays, luminescence assays, chemiluniescence assays and mass spectrometry analysis such a surface-enhanced laser desorption and ionization (SELDI) electrospray ionization (ESI), matrix assisted laser-desorption ionization (MALDI), fourier transform Ion cyclotron resonance mass spectroscopy (FTICR) alone or in combination with non-specific binding agents such as chromatography formats are also feasible. See for example, Golemis, E and Howard G. (supra).

Conveniently, an antibody can be fixed to a solid substrate to facilitate washing and isolation of the GHRsp/antibody complex. Binding of antibodies to a solid support can be achieved using known art techniques. See for example Handbook of Experimental Immunology, 4th edition, Blackwell Scientific Publications, Oxford (1986). Useful solid substrates for antibodies include glass, nylon, paper and plastics. Similarly, GHRsp can be adsorbed onto a solid substrate such as adsorbent silica, or resin particles, or silicon chips optionally coated or derivatised with ion exchange, reverse phase (eg C18 coating) or other materials. The substrate may be in the form of beads, plates, tubes, sticks or biochips. Examples of biochips include CIPHERGEN™, PROTEINCHIP™ arrays (Ciphergen Biosystems (CA, USA)), and Packard BIOCHIPS™ available from Perkin Elmer, USA. See also U.S. Pat. No. 6,225,047, U.S. Pat. No. 6,329,209. The biochips may include a chromatographic surface. Biochips or plates with addressable locations and discreet microtitre plates are particularly useful.

Also preferred for use are multiplex systems where beads containing antibodies directed to multiple analytes are used to measure levels of the analytes in a single sample. Analytes to be measured may include other markers as well as GHRsp or antigenic variants or fragments thereof. One example of a suitable multiplex bead system for use herein is the Luminex FLUOROKINE™ Multianalyte Profiling system.

Antibody assay methods are well known in the art see for example U.S. Pat. No. 5,221,685, U.S. Pat. No. 5,310,687, U.S. Pat. No. 5,480,792, U.S. Pat. No. 5,525,524, U.S. Pat. No. 5,679,526, U.S. Pat. No. 5,824,799, U.S. Pat. No. 5,851,776, U.S. Pat. No. 5,885,527, U.S. Pat. No. 5,922,615, U.S. Pat. No. 5,939,272, U.S. Pat. No. 5,647,124, U.S. Pat. No. 5,985,579, U.S. Pat. No. 6,019,944, U.S. Pat. No. 6,113,855, U.S. Pat. No. 6,143,576 and for unlabelled assays U.S. Pat. No. 5,955,377, and U.S. Pat. No. 5,631,171 see also Zola, Monoclonal Antibodies: A Manual of Techniques pp 147-158 (CRC Press, Inc 1987), Harlow and Lane (1998) Antibodies, A Laboratory Manual, Cold Spring Harbour Publications, New York, and US 2005/0064511 for a description of assay formats and conditions. All of the above references are incorporated herein by reference in their entirety.

Immunoassay analysers are also well known and include Beckman Access, Abbott AxSym, Roche ElecSys and Dade Behring Status systems amongst others which are well described[22].

Binding of a GHRsp fragment biomarker and an antibody to form a complex can be detected directly or indirectly. Direct detection is carried out using labels such as fluorescence, luminescence, radionuclides, metals, dyes and the like. Indirect detection includes binding detectable labels such as digoxin or enzymes such as horseradish peroxidase and alkaline phosphatase to form a labelled antibody followed by a step of detecting the label by addition of detection reagents.

Horseradish peroxidase for example can be incubated with substrates such as o-Phenylenediamine Dihyhydrochloride (OPD) and peroxide to generate a coloured product whose absorbance can be measured, or with luminol and peroxide to give chemiluminescent light which can be measured in a luminometer as is known in the art. Biotin or digoxin can be reacted with binding agents that bind strongly to them. For example, the proteins avidin and streptavidin will bind strongly to biotin. A further measurable label is then covalently bound or linked thereto either by direct reaction with the protein, or through the use of commonly available crosslinking agents such as MCS and carbodiimide, or by addition of chelating agents.

Generally, the complex is separated from the uncomplexed reagents for example by centrifugation. If the antibody is labelled, the amount of complex will be reflected by the amount of label detected. Alternatively, a GHRsp fragment biomarker may be labelled by binding to an antibody and detected in a competitive assay by measuring a reduction in bound labelled GHRsp fragment biomarker when the antibody-labelled-GHRsp fragment biomarker is incubated with a biological sample containing unlabelled GHRsp fragment biomarker. Other immunoassays may be used for example a sandwich assay.

In one embodiment, following contact with the antibody, usually overnight for 18 to 25 hours at 4° C., or for 1 to 2 to 4 hours at 25° C. to 40° C., the labelled GHRsp fragment biomarker bound to the binding agent (antibody) is separated from the unbound labelled GHRsp fragment biomarker. In solution phase assays, the separation may be accomplished by addition of an anti gamma globulin antibody (second-antibody) coupled to solid phase particles such as cellulose, or magnetic material. The second-antibody is raised in a different species to that used for the primary antibody and binds the primary antibody. All primary antibodies are therefore bound to the solid phase via the second antibody. This complex is removed from solution by centrifugation or magnetic attraction and the bound labelled peptide measured using the label bound to it. Other options for separating bound from free label include formation of immune complexes, which precipitate from solution, precipitation of the antibodies by polyethyleneglycol or binding free labelled peptide to charcoal and removal from solution by centrifugation of filtration. The label in the separated bound or free phase is measured by an appropriate method such as those presented above.

Competitive binding assays can also be configured as solid phase assays that are easier to perform and are therefore preferable to those above. This type of assay uses plates with wells (commonly known as ELISA or immunoassay plates), solid beads or the surfaces of tubes. The primary antibody is either adsorbed or covalently bound to the surface of the plate, bead or tube, or is bound indirectly through a second anti gamma globulin or anti Fc region antibody adsorbed or covalently bound to the plate. Sample and labelled peptide (as above) are added to the plate either together or sequentially and incubated under conditions allowing competition for antibody binding between GHRsp in the sample and the labelled peptide. Unbound labelled peptide can subsequently be aspirated off and the plate rinsed leaving the antibody bound labelled peptide attached to the plate. The labelled peptide can then be measured using techniques described above.

Sandwich type assays have greater specificity, speed and greater measuring range. In this type of assay an excess of the primary antibody to a GHRsp fragment biomarker is attached to the well of an ELISA plate, bead or tube via adsorption, covalent coupling, or an anti Fc or gamma globulin antibody, as described above for solid phase competition binding assays. Sample fluid or extract is contacted with the antibody attached to the solid phase. Because the antibody is in excess this binding reaction is usually rapid. A second antibody to the GHRsp fragment biomarker is also incubated with the sample either simultaneously or sequentially with the primary antibody. This second antibody is chosen to bind to a site on a GHRsp fragment biomarker that is different from the binding site of the primary antibody. These two antibody reactions result in a sandwich with the GHRsp fragment biomarker from the sample sandwiched between the two antibodies. The second antibody is usually labelled with a readily measurable compound as detailed above for competitive binding assays. Alternatively a labelled third antibody which binds specifically to the second antibody may be contacted with the sample. After washing away the unbound material the bound labelled antibody can be measured and quantified by methods outlined for competitive binding assays.

A dipstick type assay may also be used. These assays are well known in the art. They may for example, employ small particles such as gold or coloured latex particles with specific antibodies attached. The liquid sample to be measured may be added to one end of a membrane or paper strip preloaded with the particles and allowed to migrate along the strip. Binding of the antigen in the sample to the particles modifies the ability of the particles to bind to trapping sites, which contain binding agents for the particles such as antigens or antibodies, further along the strip. Accumulation of the coloured particles at these sites results in colour development are dependent on the concentration of competing antigen in the sample. Other dipstick methods may employ antibodies covalently bound to paper or membrane strips to trap antigen in the sample. Subsequent reactions employing second antibodies coupled to enzymes such as horse radish peroxidase and incubation with substrates to produce colour, fluorescent or chemiluminescent light output will enable quantitation of antigen in the sample.

As discussed in the following examples, in one embodiment radioimmunoassay (RIA) is the laboratory technique used. In one RIA a radiolabelled antigen and unlabelled antigen are employed in competitive binding with an antibody. Common radiolabels include $^{125}$I, $^{131}$I, $^{3}$H, and $^{14}$C.

Radioimmunoassays involving precipitation of a GHRsp fragment biomarker with a specific antibody and radiolabelled antibody binding protein can measure the amount of labelled antibody in the precipitate as proportional to the amount of the GHRsp fragment biomarker in the sample. Alternatively, a labelled GHRsp fragment biomarker is produced and an unlabelled antibody binding protein is used. A biological sample to be tested is then added. The decrease in counts from the labelled GHRsp fragment biomarker is proportional to the amount of GHRsp fragment biomarker in the sample.

In RIA it is also feasible to separate bound GHRsp fragment biomarkers from free GHRsp fragment biomarkers. This may involve precipitating the GHRsp fragment biomarker/antibody complex with a second antibody. For example, if the GHRsp fragment biomarker/antibody complex contains rabbit antibody then donkey anti-rabbit antibody can be used to precipitate the complex and the amount of label counted. For example in an LKB, Gammamaster counter. See Hunt P J, et al., Immunoreactive amino terminal pro brain natriuretic peptide (NT-proBNP): a new marker of cardiac impairment. *Clin. Endocrinol.* 1997 47:287-296.

The methods of the invention further comprise measuring the levels of one or more other markers of pneumonia, acute decompensated heart failure (ADHF) or a combination of pneumonia and ADHF that are not a GHRsp fragment biomarker. The level of the other marker or markers can be compared to mean control levels from a control population. A deviation in the measured level from the mean control level is diagnostic of pneumonia.

The methods of the invention have been described with respect to higher levels or increase in GHRsp fragment biomarker levels being indicative of pneumonia. Measuring deviations above or below a control level are also contemplated.

The methods of the invention have also been described with respect to higher levels or increase in GHRsp fragment biomarker levels being indicative of acute decompensated heart failure or indicative of pneumonia and acute decompensated heart failure. Measuring deviations above or below a control level are also contemplated.

Correlating the level of GHRsp fragment biomarker with other markers can increase the predictive, diagnostic or monitoring value of GHRsp fragment biomarkers. In the case of pneumonia, acute decompensated heart failure or a scenario where a subject has both pneumonia and acute decompensated heart failure, combining GHRsp fragment biomarker levels with known biomarkers of pneumonia and acute decompensated heart failure can increase the diagnostic value of a patient outcome.

Examples of known biomarkers of pneumonia and acute decompensated heart failure include, but are not limited to, brain natriuretic protein (BNP), NT-proBNP, C-reactive protein (CRP), blood urea nitrogen (BUN), procalcitonin (PCT), pancreatic stone protein and Troponin.

Analysis of a number of peptide markers can be carried out simultaneously or separately using a single test sample. Simultaneous, two or multi-site format assays are preferred. Multiplex bead, microassay or biochip systems are particularly useful. The beads, assays or chips can have a number of discreet, often addressable locations, comprising an antibody to one or more markers including GHRsp and GHRsp fragments. The one or more markers include more than one GHRsp fragment biomarker. For example, it may be useful to assay for N-terminal and C-terminal GHRsp fragment biomarker fragments and combine the assay results. Many other such marker combinations are feasible. US2005/0064511, U.S. Pat. No. 6,019,944, and Ng and Ilang, J. Cell Mol. Med., 6:329-340 (2002) provide a description of microarray, chips, capillary devices and techniques useful in the present invention. Luminex provides a multiplex bead system useful in the present invention. See also The Protein Protocols Handbook, supra. Laboratory analysers suitable for use with separate or sequential assays include AxSym (Abbott, USA), ElecSys (Roche), Access (Beckman), ADVIA CENTAUR® (Bayer) and Nichols Advantage® (Nichols Institute) immunoassay system.

In one embodiment simultaneous assays of a plurality of polypeptides are performed on a single surface such as a chip or array.

In another embodiment separate assays of one or more non-GHRsp markers are performed and the results collated or combined with GHRsp fragment biomarker results.

Where a subject is to be monitored, a number of biological samples may be taken over time. Serial sampling allows changes in marker levels, particularly GHRsp fragment biomarkers to be measured over time. Sampling can provide information on the approximate onset time of an event, the severity of the event, indicate which therapeutic regimes may be appropriate, response to therapeutic regimes employed, or long term prognosis. Analysis may be carried out at points of care such as in ambulances, doctors offices, on clinical presentation, during hospital stays, in outpatients, or during routine health screening.

The methods of the invention may also be performed in conjunction with an analysis of one or more risk factors such as but not limited to age, weight, level of physical activity and family history of events. Test results can also be used in conjunction with the methods of the invention. For example, glucose tolerance tests, ECG results and clinical examination. A statistically significant change in circulating level of GHRsp, together with one or more additional risk factors or test results may be used to more accurately diagnose, prognose or monitor the subject's condition.

The methods herein can also be used as a guide to therapy. For example what therapies to initiate and when, therapy monitoring, detection of positive or adverse effects of therapy, and adjustment of therapeutic regimes if and when required dependent on results. This can improve short, medium and long term outcomes for patients.

In another embodiment, the invention provides GHRsp (1-10) (SEQ ID NO:4), a novel peptide discovered and isolated by Applicants. Thus, also provided are isolated and/or purified GHRsp (1-10) (SEQ ID NO:4) peptides (including human GHRsp (1-10) (SEQ ID NO:4) and species variants thereof). Also included are GHRsp (1-10) (SEQ ID NO:4) binding agents including anti-GHRsp (1-10) (SEQ ID NO:4) antibodies and antibody binding fragments, assays for GHRsp (1-10) (SEQ ID NO:4) including immunoassays and their use in the detection of GHRsp (1-10) (SEQ ID NO:4) in a biological sample, as described herein. GHRsp (1-10) (SEQ ID NO:4) binding agents and assays are useful in diagnosing, assessing, monitoring, etc., a biological event or disorder which correlates with the release of a GHRsp (1-10) (SEQ ID NO:4) fragment into the circulation. Such events or disorders include pneumonia, as described herein, and can be used can be used for the diagnosis, prognosis, risk stratification, assessing, staging, monitoring, categorizing and determination of further diagnosis and treatment regimens in subjects with pneumonia or suspected pneumonia.

Pneumonia

Figure 4:
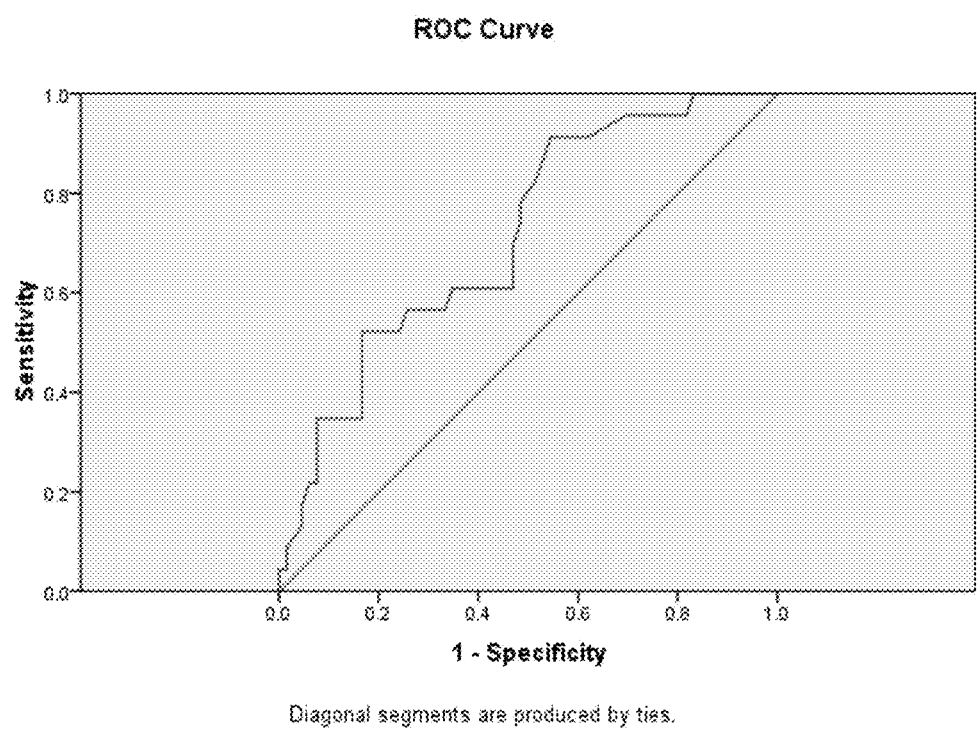
FIG. 4 shows the results of a radioimmunoassay demonstrating that GHRsp (1-9) immunoreactivity in blood shows significant correlation with pneumonia in human subjects, with a ROC of 0.714. These data are based on n=23 patients with confirmed pneumonia infection from an initial cohort of 123 human patients sampled.

Applicants have shown that levels of GHRsp fragment biomarkers are correlated with pneumonia infection (FIG. 4). Applicants have therefore provided a useful early and specific marker for pneumonia. This will allow the early diagnosis of pneumonia and allow a physician to distinguish such cases from other infections as well as from other causes of breathlessness. This significantly shortens the window currently experienced waiting for other tests. A more precise diagnosis and treatment can therefore be effected earlier, reducing morbidity and mortality and giving better prognostic outcomes. GHRsp testing to accelerate diagnosis allows prompt introduction of treatment. Effectiveness of treatment can also be monitored by repeat testing, and therapy adjusted as appropriate.

The presence of GHRsp fragment biomarker is preferably detected in the sample by binding GHRsp fragment biomarker to a binding agent such as an antibody, including an antibody of the invention and measuring the presence of the amount of bound GHRsp fragment biomarker.

As noted above, antibodies which bind or selectively bind GHRsp including antigenic variants and fragments thereof, form a further aspect of the invention and the antibodies may be prepared by the techniques discussed above. The antibodies are useful in the methods and assays of the invention.

In a further aspect, the invention provides a kit for diagnosing, assessing or monitoring pneumonia in a subject, comprising an GHRsp fragment biomarker binding agent (or binding agents for multiple GHRsp fragment biomarkers) including an antibody or antigen-binding fragment of the invention. When the kit is for use in diagnosing, the biological sample is in one embodiment, for example, obtained from a subject within and one or more additional samples may be taken and analyzed periodically. The kit may be calibrated to measure GHRsp levels in the range of at least about 0.1 pmol/L, at least about 1 pmol/L, at least about 5 pmol/L, at least about 10 pmol/L, or other levels.

Calibration of assays can be effected according to known art techniques, for example using blood samples with known levels of GHRsp fragment biomarker, or a set of calibrates with different known levels of GHRsp in each. Test strips for use in diagnostic kits are commonly calibrated during manufacture. See for example U.S. Pat. No. 6,780,645. The kit is useful for measuring the level of GHRsp fragment biomarker in a biological sample. The detection reagents may be oligonucleotide sequences complementary to GHRsp or a fragment of the GHRsp marker, or antibodies which bind to the polypeptides encoded by the marker. The reagents may be bound to a solid matrix as discussed above or packaged with reagents for binding them to the matrix. The solid matrix or substrate may be in the form of beads, plates, tubes, dip sticks, strips or biochips all as discussed above.

Detection reagents include wash reagents and reagents capable of detecting bound antibodies (such as labelled secondary antibodies), or reagents capable of reacting with the labelled antibody.

The kit may also conveniently include a control reagent (positive and/or negative) and/or a means for detecting the polypeptide or antibody. Instructions for use may also be included with the kit, such as taking a biological sample from a subject within six, four or two hours of onset or presentation with pneumonia, measuring the level of GHRsp in the sample, comparing same to a control level and associating the result with pneumonia infection status. Generally an increase in the GHRsp marker level from a control is indicative of pneumonia.

Most usually, the kits will be formatted for assays known in the art, and in one embodiment for PCR, Northern hybridization or Southern ELISA assays, as are known in the art.

The kits may also include one or more additional assays (or instructions for use of additional assays) for targets or markers indicative of pneumonia. These include procalcitonin, Triggering receptor expressed on myeloid cells-1 (TREM-1), C-reactive protein, immunoglobulins, and proinflammatory cytokines. They may also include one or more GHRsp fragment biomarkers in combination an assay or assays for one or more of copeptin, cortisol, endotoxin and/or proadrenomedullin. In one embodiment, the GHRsp fragment biomarker is GHRsp (1-9) (SEQ ID NO:3). In another embodiment, the GHRsp fragment biomarker is GHRsp (1-9) (SEQ ID NO:3). In another embodiment, the GHRsp fragment biomarker is GHRsp (1-9) and GHRsp (1-10) (SEQ ID NO:4).

The kit will be comprised of one or more containers and may also include collection equipment, for example, bottles, bags (such as intravenous fluids bags), vials, syringes, and test tubes. At least one container holds a product which is effective for diagnosing or monitoring pneumonia. The product is usually a nucleic acid molecule, polypeptide or a binding agent, particularly an antibody or antigen-binding fragment, or a composition comprising any of these. In a preferred embodiment, an instruction or label on, or associated with, the container indicates that the composition is used for diagnosing or monitoring pneumonia. Other components may include needles, diluents and buffers. Usefully, the kit may include at least one container comprising a buffer, such as phosphate-buffered saline, Ringer's solution and dextrose solution.

Binding agents that bind or selectively bind a GHRsp fragment biomarker (and optionally a non-GHRsp fragment biomarker) are desirably included in the kit. In one embodiment, the binding agent is an antibody, preferably an antibody or antigen-binding fragment of the invention. The antibody used in the assays and kits may be in one embodiment monoclonal or polyclonal and may be prepared in any mammal as discussed above. The antibodies may be prepared against a native GHRsp fragment biomarker peptide sequence of the invention, for example, GHRsp (1-9) (SEQ ID NO:3) and/or GHRsp (1-10) (SEQ ID NO:4), or a synthetic peptide based on, or including same, or may be raised against an exogenous sequence alone or fused to another sequence.

In one kit embodiment a GHRsp fragment biomarker detection reagent is immobilized on a solid matrix such as a porous strip or chip to form at least one GHRsp fragment biomarker detection site. The measurement or detection region of the porous strip may include a plurality of detection sites, such detection sites containing a GHRsp fragment biomarker detection reagent. The sites may be arranged in a bar, cross or dot or other arrangement. A test strip or chip may also contain sites for negative and/or positive controls. The control sites may alternatively be on a different strip or chip. The different detection sites may contain different amounts of immobilized nucleic acids or antibodies, e.g., a higher amount in the first detection site and lower amounts in subsequent sites. Upon the addition of a test biological sample the number of sites displaying a detectable signal provides a quantitative or semi-quantitative indication of the amount of GHRsp fragment biomarker present in the sample.

Also included in the kit may be a device for sample analysis comprising a disposable testing cartridge with appropriate components (markers, antibodies and reagents) to carry out sample testing. The device will conveniently include a testing zone and test result window. Immunochromatographic cartridges are examples of such devices. See for example U.S. Pat. No. 6,399,398; U.S. Pat. No. 6,235,241 and U.S. Pat. No. 5,504,013.

Alternatively, the device may be an electronic device which allows input, storage and evaluation of levels of the measured marker against control levels and other marker levels. US 2006/0234315 provides examples of such devices. Also useful in the invention are Ciphergen's Protein Chip® which can be used to process SELDI results using Ciphergen's Protein Chip® software package.

Acute Decompensated Heart Failure (ADHF)

Chronic stable heart failure may easily decompensate leading to acute decompensated heart failure (ADHF). ADHF is a worsening of the symptoms, typically shortness of breath (dyspnea), edema and fatigue, in a patient with existing heart disease. It is a common and potentially serious cause of acute respiratory distress, and its most sensitive clinical sign is jugular venous distension. Brain natriuretic peptide (BNP) is a well documented and used biomarker for the diagnosis of ADHF, where elevated levels in blood relative to a control or reference level is diagnostic of this condition.

Pneumonia and Acute Decompensated Heart Failure (ADHF)

The accurate and rapid detection of acutely decompensated heart failure (ADHF) or pneumonia (or both) as the cause for breathlessness is important and large time consuming problem for emergency department doctors and general practitioners. This is because inaccurate or incomplete diagnosis coupled with resultant incorrect treatment can be fatal, due to incorrect treatment or time delays to instituting correct treatment.

Currently, there is no single biomarker or panel of biomarkers that can diagnose whether a patient has pneumonia and ADHF. This is vitally important as the diagnosis of pneumonia is often missed in patients with diagnosed ADHF, a situation which severely compromises the effective treatment of such patients, and can prove fatal. As shown in the examples which follow, the Applicants are first to deomonstrate the usefulness of GHRsp fragments as reliable and predictable circulating biomarkers of pneumonia and ADHF.

A further understanding of the invention will be gained by reference to the following non-limiting experimental section which is illustrative and is not intended to limit the invention or the claims in any way. The data support the use of the compounds and compositions described herein for diagnosing, assessing or monitoring pneumonia in a subject.

EXAMPLES

Methods

All human protocols were approved by the Upper South Regional Ethics Committee of the Ministry of Health, New Zealand and were performed in accord with the Declaration of Helsinki.

Chemicals

Synthetic human GHR signal peptide GHRsp (1-9), (SEQ ID NO:3) was synthesised by Mimotopes (Australia) using a mild Fmoc Solid Phase Synthesis method. All buffer reagents were purchased from BDH® (UK) and/or Sigma (Mo, USA). GHRsp(1-9) (SEQ ID NO:3) was synthesised with the C-terminal extended with cysteine for directional carrier coupling. GHRsp(1-9) was also C-terminally extended with a tyrosyl residue for tracer preparation on the same peptide.

Human Studies

For this study, blood samples were initially obtained from 123 patients presenting to the Emergency Department of Christchurch Hospital with the primary complaint of breathlessness/dyspnoea.

Patients were eligible for this study if they are ≥18 years of age and provide acute attendance at Christchurch Hospital ED with a primary complaint of shortness of breath. Patients were excluded if they could not provide informed consent or if there was clear trauma-related shortness of breath (e.g. crush injury or penetrating wounds). For those patients meeting the inclusion criteria and having provided informed consent, the following information was gathered: presenting complaint, past medical history, physical examination with particular emphasis on cardiovascular and respiratory findings, routine biochemistry and haematology and cardiac injury markers if ordered by the ED, chest x-ray and echocardiography (if available).

Blood samples were then taken into tubes on ice and centrifuged at +4° C. at 2700 g for 5 min and the plasma stored at −80° C. until analysed.

Plasma Extraction

All plasma samples were extracted on SepPak Cartridges, (Waters, USA) as previously described (Hunt P3, et al., Immunoreactive amino terminal pro brain natriuretic peptide (NT-proBNP): a new marker of cardiac impairment. *Clin. Endocrinol.* 1997 47:287-296), dried and stored at −20° C. prior to RIA and HPLC.

Hormone Concentration Analysis

Plasma samples were assayed for GHRsp was measured by specific RIA as follows:

GHRsp RIA

For the measurement of human GHRsp fragment biomarker peptides, a RIA directed against amino acids 1-9 (SEQ ID NO:3) of the human preproghrelin (1-23) signal sequence (SEQ ID NO:1).

Antibody Generation preproGHR(1-9)$^{Cys10}$ was coupled to malemide treated N-e-maleimidocaproyloxy succinimide ester (EMCS) derivatised BSA in PBS (pH 7.0) by gentle mixing at room temperature. Coupled peptide was emulsified with Freund's (2 ml) adjuvant and injected subcutaneously (2 ml total) in 2 New Zealand white rabbits over 4-5 sites at monthly intervals. Rabbits were bled 12 days after injection to assess antibody titres until adequate levels were achieved. For RIA, GHRsp IR was determined using antiserum at a final dilution of 1:15,000. This antiserum had no detectable cross reactivity with peptides and drugs indicated in FIG. 3, including human proBNP (1-13), proBNP (1-76), proANP (1-30), insulin, angiotensin II, angiotensin (1-7), urotensin II, CNP, ghrelin, C-ghrelin, proCNP (52-117), proCNP (1-15), adrenomedulin, urocortin I, urocortin II, BNP-SPn(1-10), ANP-SPc (16-25), ANP-SP (1-10), INS-SPn (1-9). Cross reactivity was assessed following Klee, G G, Interference in hormone immunoassays *Clin Lab Bed*, 2004, 24:1-18.

Iodination and Assay Method

GHRsp(1-9)$^{Try10}$ was iodinated via the Chloramine T method and purified on reverse phase HPLC(RP-HPLC) as previously described. Brennan et al., "Preparation of bispecific antibodies by chemical recombination of monoclonal immunoglobulin G1 fragments" *Science* 229:81-83 (1985). From this preparation an iodinated tracer form after RP-HPLC was tested. All samples, standards, radioactive traces and antiserum solutions were diluted in potassium based assay buffer. Hunt P J, et al., Immunoreactive amino terminal pro brain natriuretic peptide (NT-proBNP): a new marker of cardiac impairment. *Clin. Endocrinol.* 1997 47:287-296. The assay incubate consisted of 100 μL sample or standard (0-640 pmol human preproGHR(1-9) combined with 100 μL antiserum which was vortexed and incubated at 4° C. for 24 hours. 100 μL of trace (4000-5000 cpm) was then added and further incubated for 24 hours at 4° C. Free and bound immunoreactivities were finally separated by solid phase second antibody method (donkey anti-sheep Sac-Cel®, IDS Ltd, England) and counted in a Gammamaster counter (LKB, Uppsala, Sweden Statistical Analysis All results are presented as mean±SEM. Time-course data were analysed using two-way ANOVA for repeated measurements followed by least significant difference post-hoc testing. Correlation analysis of plasma hormone concentrations was carried out using a general linear regression model. In all analyses, a P-value <0.05 was considered significant.

Results

To determine if the 1-9 amino acid fragment of ghrelin signal peptide is present in circulation of humans, a specific radioimmunoassay (RIA) directed against residues 1-9 of preproghrelin(1-23) was used. Dilution of plasma extracts demonstrate parallelism with the standard curve (not shown). Of the initial 123 patients tested, 23 had pneumonia as determined by clinical workup, chest X-ray and confirmatory sputum analysis for *Pneumococcus* strain.

Median plasma concentrations of GHRsp (1-9) in the non-infected patients (without pneumonia) were determined as 8.8 pmol/L (n=100). Median plasma concentrations of GHRsp (1-9) in the infected patients (with pneumonia) were determined as 11.1 pmol/L (n=23). An ROC curve of these results is presented in FIG. 4, with an AUC of 0.714 (P<0.01).

Of a total of 286 patients tested, 52 had confirmed pneumonia infection as determined by clinical workup, chest X-ray and confirmatory sputum analysis for Pneumococcus strain. This includes the n=23 patients from the initial analysis referred to above (FIG. 4).

Figure 5:
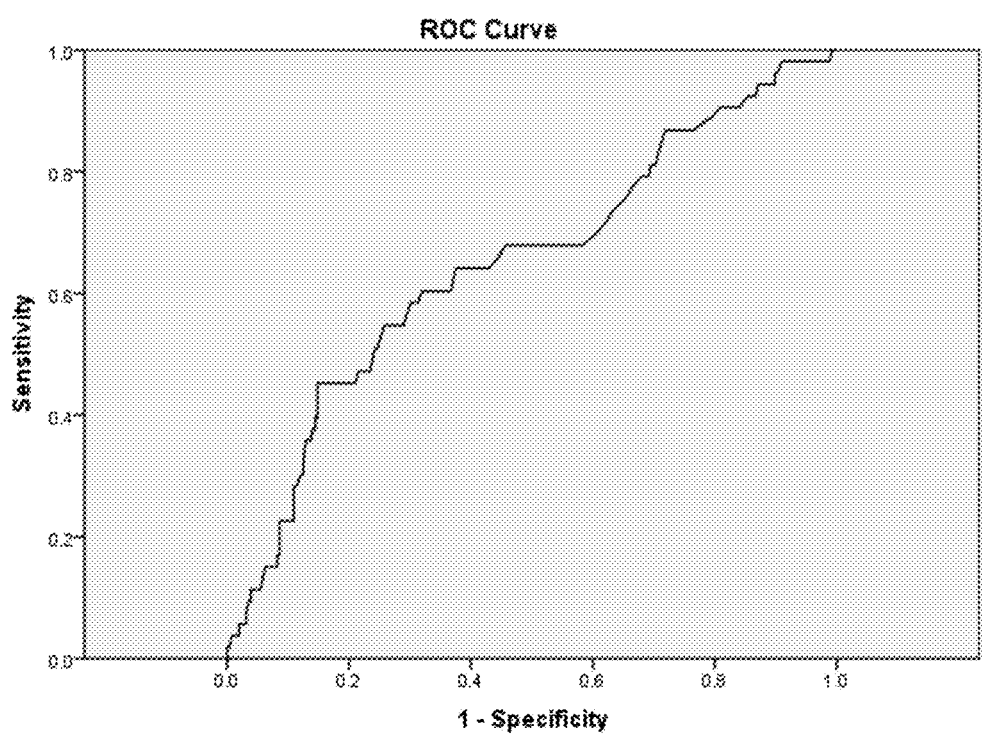
FIG. 5 shows the results of a radioimmunoassay demonstrating that GHRsp (1-9) (SEQ ID NO:3) immunoreactivity in blood shows significant correlation with pneumonia in human subjects, with a ROC of 0.654. These data are based on n=52 patients with confirmed pneumonia infection (which comprises the 23 patients from the initial human patient cohort.

Median plasma concentrations of GHRsp (1-9) (SEQ ID NO:3) in the non-infected patients (without pneumonia) were determined as 11.1 pmol/L. Median plasma concentrations of GHRsp (1-9) (SEQ ID NO:3) in the infected patients (with pneumonia) were determined as 17.8 pmol/L (n=52). An ROC curve of these results is presented in FIG. 5, with an AUC of 0.654 (P<0.001).

These data also reveal a specificity of 85.2% and a sensitivity of 45.3% at >18.9 pmol/L for GHRsp in patients who had pneumonia infection.

Further, of a total of 286 patients tested, 117 had confirmed acute decompensated heart failure as determined by clinical work up (e.g. presence of a jugular venous distension) as well as the presence of BNP in circulation at a level that is higher than the level in a control or reference sample.

Median plasma concentrations of GHRsp (1-9) (SEQ ID NO:3) in the non-affected patients (i.e. without acute decompensated heart failure) were again determined as 11.1 pmol/L. Median plasma concentrations of GHRsp (1-9) (SEQ ID NO:3) in the ADHF patients were determined as 16.1 pmol/L (n=117). An ROC curve of these results is presented in FIG. 6, with an AUC of 0.601 (P<0.01).

These data also reveal a specificity of 82.3% and a sensitivity of 26.5% at >18.9 pmol/L for GHRsp in patients who had acute decompensation heart failure.

Finally, of a total of 286 patients tested, 8 were confirmed to have both pneumonia and acute decompensated heart failure (ADHF) as determined by routine clinical workup, chest X-ray and confirmatory sputum analysis for *Pneumococcus* strain in the case of pneumonia infection, and as determined by routine clinical work-up (e.g. presence of a jugular venous distension), as well as the presence of BNP in circulation at a level that is higher than the level in a control or reference sample, in the case of acute decompensated heart failure.

Median plasma concentrations of GHRsp (1-9) (SEQ ID NO:3) in the non-infected/non-affected patients (i.e. without penumonia and acute decompensated heart failure) were determined as 11.1 pmol/L. Median plasma concentrations of GHRsp (1-9) (SEQ ID NO:3) in those patients with pneumonia and acute decompensated heart failure were determined as 19.75 pmol/L (n=8). An ROC curve of these results is presented in FIG. 6, with an AUC of 0.751 (P<0.001).

These data also reveal a specificity of 80.6% and a sensitivity of 75.0% at >18.9 pmol/L for GHRsp in patients who had pneumonia and acute decompensated heart failure.

Figure 6:
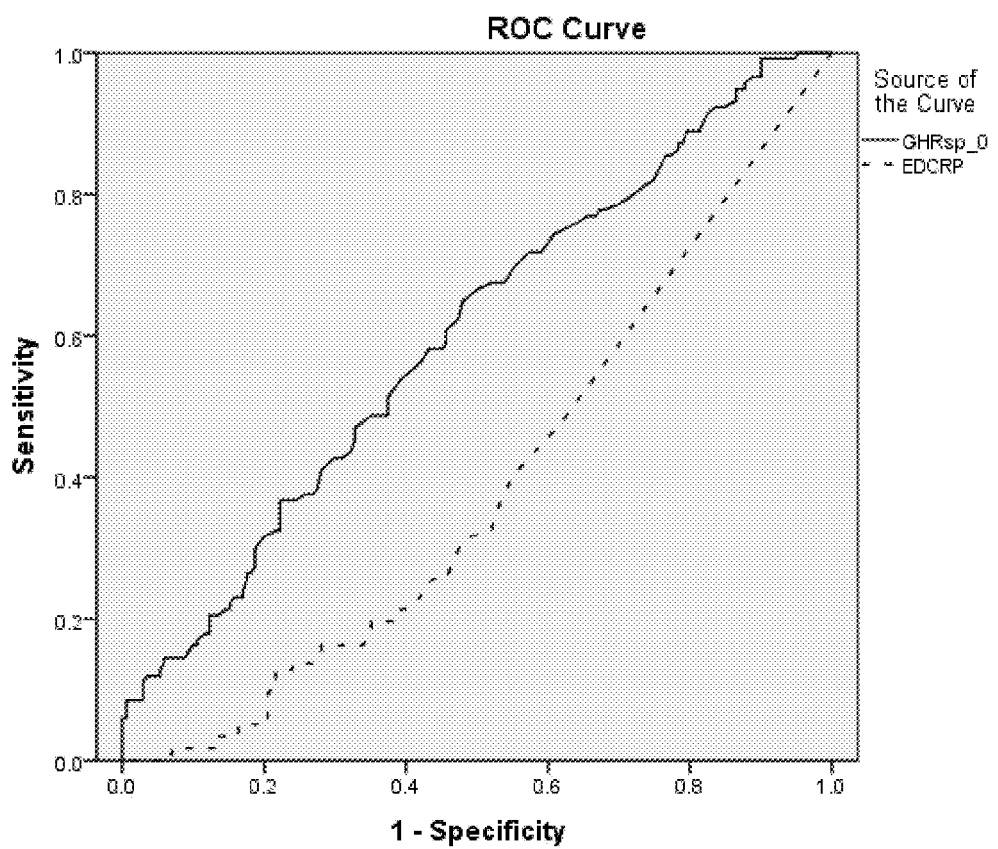
FIG. 6 shows the results of a radioimmunoassay demonstrating that GHRsp (1-9) (SEQ ID NO:3) immunoreactivity in blood shows significant correlation with acute decompensated heart failure (ADHF), with a ROC of 0.601. Also shown is the ROC curve for C-reactive protein (CRP).
Figure 7:
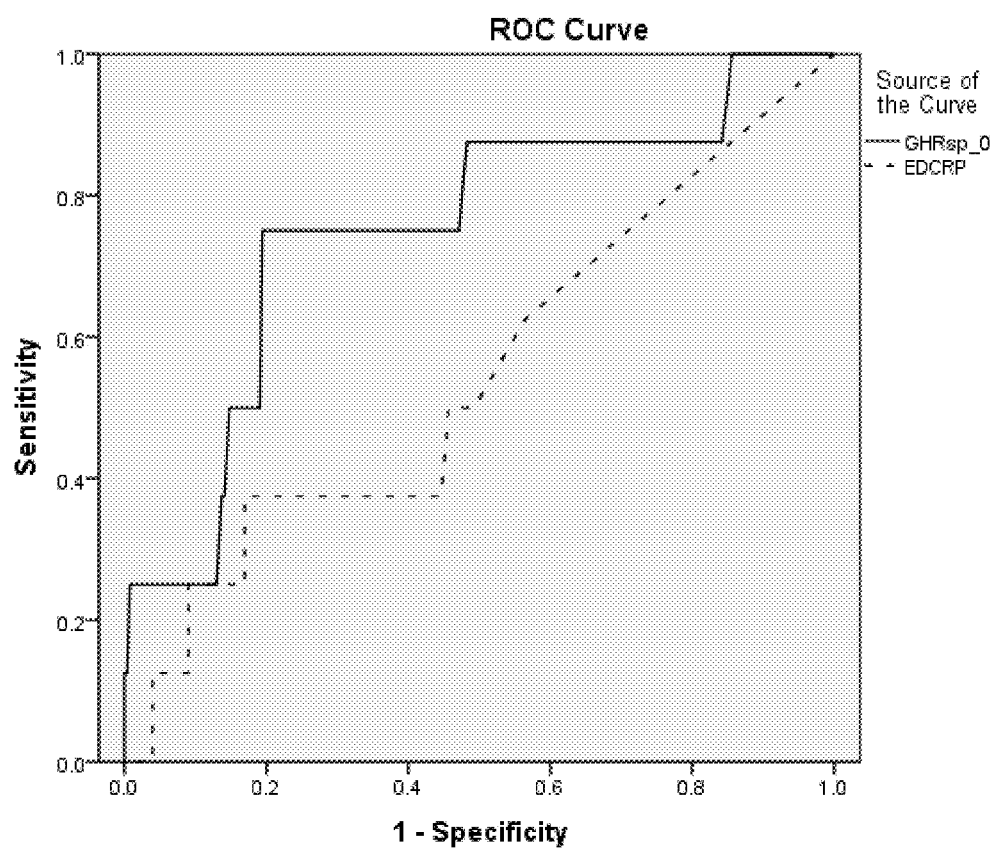
FIG. 7 shows the results of a radioimmunoassay demonstrating that GHRsp (1-9) (SEQ ID NO:3) immunoreactivity in blood shows significant correlation with pneumonia and acute decompensated heart failure (ADHF), with a ROC of 0.751. Also shown is the ROC curve for C-reactive protein (CRP).

Also shown in FIGS. 6 and 7 are the ROC curves for C-reactive protein (CRP), a known biomarker of inflammation. With an ROC AUC of 0.409 (P<0.001) for CRP with a specificty of 74.2% and a sensitivity of 15.8% in acute decompensated heart failure (ADHF) for GHRsp (1-9) (SEQ ID NO:3) at 31.5 mg/L, and a ROC AUC of 0.561 (P<0.001) for CRP with a specificity of 78.4% and a sensitivity of 37.5% in pneumonia and ADHF for GHRsp (1-9) (SEQ ID NO:3) at 31.5 mg/L, comparatively these data demonstrate the superior clinical utility of GHRsp fragments as a biomarker of pneumonia and ADHF as well as ADHF.

Unless otherwise stated, the plasma levels of GHRsp were measured immediately following presentation of the patient to the emergency department.

CONCLUSION

This evidence is the first to document that signal peptide fragments from preproghrelin are present and significantly elevated in the circulation of patients with pneumonia. With a ROC AUC measurement of 0.714 (p<0.01) (n=23), Applicants demonstrate that measurement of GHRsp (1-9) (SEQ ID NO:3) in blood is useful as a rapid biomarker of pneumonia. Further data supports that GHRsp (1-10) (SEQ ID NO:4) was also detected in blood from pneumonia patients.

From the ROC curve, the results also show 83% specificity/48% sensitivity at 11.1 pmol/L, and 92% specificity/35% sensitivity at 13.1 pmol/L. These data confirm the suitability of the GHRsp fragment assay as a meaningful decision making tool and representing a good level of clinical usefulness.

The significance of these data was further confirmed when the patient cohort was expanded to include a total of 286 patients tested of which n=52 had confirmed pneumonia infection. For the avoidance of doubt, the n=52 with confirmed pneumonia infection includes n=23 from the initial measurements. With a ROC AUC measurement of 0.654 (p<0.001), a specificity of 85.2% and a sensitivity of 45.3% at >18.9 pmol/L for GHRsp (1-9) (SEQ ID NO:3), Applicants further demonstrate that measurement of GHRsp (1-9) (SEQ ID NO:3) in blood is useful as a rapid biomarker of pneumonia.

Applicants also present evidence to show that signal peptide fragments from preproghrelin are present and significantly elevated in the circulation of patients with acute decompensated heart failure (ADHF), as well in patients with both pneumonia and acute decompensated heart failure (ADHF).

With a ROC AUC measurement of 0.601 (P<0.01) (n=117), a specificity of 82.3% and a sensitivity of 26.5% at >18.9 pmol/L for GHRsp (1-9) (SEQ ID NO:3), Applicants show that measurement of GHRsp (1-9) (SEQ ID NO:3) in blood is useful as a rapid biomarker of acute decompensated heart failure (ADHF).

Also, with a ROC AUC measurement of 0.751 (P<0.001) (n=8), a specificity of 80.6% and a sensitivity of 75.0% at >18.9 pmol/L for GHRsp (1-9), Applicants show that measurement of GHRsp (1-9) (SEQ ID NO:3) in blood is useful as a rapid biomarker of patients with pneumonia and acute decompensated heart failure (ADHF).

Again, these data further confirm the suitability of the GHRsp fragment assay as a meaningful decision making tool representing a good level of clinical usefulness.

The increase in GHRsp peptides (1-9) (SEQ ID NO:3) and (1-10) (SEQ ID NO:4) in response to pneumonia, acute decompensated heart failure, and in patients with pneumonia and acute decompensated heart failure, support their use as biomarkers for these indications. The measurement of GHRsp (1-9) (SEQ ID NO:3) and GHRsp (1-10) (SEQ ID NO:4) also has potential as markers of long term prognosis and outcome in patients with pneumonia, acute decompensated heart failure, and in patients with pneumonia and acute decompensated heart failure.

Those skilled in the art will of course appreciate that the above description is provided by way of example and that the invention is not limited thereto.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims.

Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of a Patent Office unless such statement is specifically and without qualification or reservation expressly adopted in a responsive writing by Applicants.

The invention claimed is:

1. A method of monitoring a subject having both pneumonia and acute decompensated heart failure, comprising
   (a) performing an immunoassay to determine a level of a ghrelin signal peptide (GHRsp) fragment by contacting a body fluid sample obtained from the subject with an antibody or antigen-binding antibody fragment thereof that binds a ghrelin signal peptide fragment that is (a) GHRsp (1-9) (SEQ ID NO:3); or (b) GHRsp (1-10) (SEQ ID NO:4) and detecting ghrelin signal peptide fragment bound to the antibody or antigen-binding antibody fragment thereof;
   (b) comparing the level of the ghrelin signal peptide fragment determined by the immunoassay with a level of the ghrelin signal peptide fragment in a reference body fluid sample obtained from the same subject at an earlier time, which reference body fluid sample contained a level of ghrelin signal peptide fragment that was above a threshold level of the ghrelin signal peptide fragment that distinguishes a population of subjects having both pneumonia and acute decompensated heart failure from a population of subjects not having both pneumonia and acute decompensated heart failure, wherein a level of ghrelin signal peptide fragment that is above the threshold level indicates the subject has both pneumonia and acute decompensated heart failure; and,
   (c) setting a treatment regimen or adjusting a treatment regimen for the subject based upon said comparing of the level of the ghrelin signal peptide fragment in the body fluid sample with the reference body fluid sample.

2. A method according to claim 1, wherein the antibody, or antigen-binding antibody fragment thereof, is immobilized on a solid support.

3. A method according to claim 1, wherein the antibody, or antigen-binding antibody fragment thereof, selectively binds GHRsp (1-9) (SEQ ID NO:3).

4. A method according to claim 1, wherein said antibody, or antigen-binding antibody fragment thereof, is a polyclonal, monoclonal, bispecific, chimeric or humanized antibody, or antigen-binding antibody fragment thereof.

5. A method according to claim 4, wherein said ghrelin signal peptide fragment or the antibody, or antigen-binding antibody fragment thereof, is labelled with a detectable marker.

6. A method according to claim 3, wherein the body fluid sample is a blood, plasma, serum, saliva, interstitial fluid, or urine sample.

7. A method according to claim 3, wherein the level of ghrelin signal peptide fragment is measured using an immunoassay selected from radioimmunoassay (RIA), enzyme-linked immunosorbent assay (ELISA) and immunofluorometric assay.

8. A method according to claim 1, wherein the body fluid sample is a blood, plasma, serum, saliva, interstitial fluid, or urine sample.

9. A method according to claim 1, wherein the level of ghrelin signal peptide fragment bound to the antibody, or antigen-binding antibody fragment thereof, is measured using mass spectroscopy.

10. An assay method for diagnosing a subject as having both acute decompensated heart failure and pneumonia, where the subject has i) one or more symptoms of pneumonia, and/or ii) one or more symptoms of acute decompensated heart failure, the assay method comprising:
    (a) contacting a body fluid sample from the subject with an antibody, or antigen-binding antibody fragment thereof, that selectively binds a ghrelin signal peptide (GHRsp) fragment that is (a) GHRsp (1-9) (SEQ ID NO:3); or (b) GHRsp (1-10) (SEQ ID NO:4);
    (b) determining a level of ghrelin signal peptide fragment bound by the antibody, or antigen-binding antibody fragment thereof; and
    (c) comparing the level of said bound ghrelin signal peptide fragment with a threshold level of the ghrelin signal peptide fragment that distinguishes a population of subjects having both pneumonia and acute decompensated heart failure from a population of subjects not having both pneumonia and acute decompensated heart failure, wherein a level of ghrelin signal peptide fragment that is above the threshold level indicates the subject has both pneumonia and acute decompensated heart failure.

11. An assay method according to claim 10, wherein the subject has one or more symptoms of pneumonia.

12. An assay method according to claim 10, wherein the subject has one or more symptoms of acute decompensated heart failure.

13. An assay method according to claim 10, wherein the body fluid sample is a blood, plasma, serum, saliva, interstitial fluid, or urine sample.

14. An assay method according to claim 10, which further comprises measuring the level of one or more non-GHRsp markers of pneumonia and acute decompensated heart failure.

15. An assay method according to claim 14 wherein the non-GHRsp marker is selected from the group consisting of procalcitonin (PCT), C-reactive protein (CRP), brain natriuretic protein (BNP), N-terminal-proBNP (NT-proBNP), blood urea nitrogen (BUN), pancreatic stone protein and Troponin.

16. An assay method according to claim 10, wherein the level of ghrelin signal peptide fragment bound to the antibody, or antigen-binding antibody fragment thereof, is measured using mass spectroscopy.

17. An assay method according to claim 12, wherein the one or more symptoms of acute decompensated heart failure are shortness of breath (dyspnea), edema and/or fatigue.

18. An assay method according to claim 10, wherein the antibody, or antigen-binding antibody fragment thereof, is immobilized on a solid support.

19. An assay method according to claim 10, wherein the antibody, or antigen-binding antibody fragment thereof, selectively binds GHRsp (1-9) (SEQ ID NO:3).

20. An assay method according to claim 10, wherein said ghrelin signal peptide fragment or the antibody, or antigen-binding antibody fragment thereof, is labelled with a detectable marker.

21. An assay method according to claim 10, wherein the level of ghrelin signal peptide fragment bound to the antibody, or antigen-binding antibody fragment thereof, is measured using an immunoassay selected from radioimmunoassay (RIA), enzyme-linked immunosorbent assay (ELISA) and immunofluorometric assay.

22. An assay method according to claim 10, wherein said antibody, or antigen-binding antibody fragment thereof, is a polyclonal, monoclonal, bispecific, chimeric or humanized antibody, or antigen-binding fragment thereof.

23. An assay method according to claim 10, wherein the body fluid sample is a blood, plasma, or serum sample.

24. An assay method according to claim 11, wherein the one or more symptoms of pneumonia is one or more of cough with sputum production, fever, pleural effusion, sharp chest pain on inspiration, and/or breathlessness.

* * * * *

UNITED STATES PATENT AND TRADEMARK OFFICE
CERTIFICATE OF CORRECTION

Page 1 of 1

PATENT NO. : 10,114,028 B2
APPLICATION NO. : 13/844449
DATED : October 30, 2018
INVENTOR(S) : Christopher Joseph Pemberton et al.

It is certified that error appears in the above-identified patent and that said Letters Patent is hereby corrected as shown below:

On the Title Page

Item (72), Fourth inventor's Name:
Please replace "Matthew Simon Byers" with --Mathew Simon Byers--

Signed and Sealed this
Nineteenth Day of March, 2019

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 117
<212> TYPE: PRT
<213> ORGANISM: Homo sapiens

<400> SEQUENCE: 1

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
                20                  25                  30

Gln Arg Val Gln Gln Arg Lys Glu Ser Lys Lys Pro Pro Ala Lys Leu
            35                  40                  45

Gln Pro Arg Ala Leu Ala Gly Trp Leu Arg Pro Glu Asp Gly Gly Gln
        50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln Gln His Ser Gln
                85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 2
<211> LENGTH: 23
<212> TYPE: PRT
<213> ORGANISM: Homo sapiens

<400> SEQUENCE: 2

Met Pro Ser Pro Gly Thr Val Cys Ser Leu Leu Leu Gly Met Leu
1               5                   10                  15

Trp Leu Asp Leu Ala Met Ala
                20

<210> SEQ ID NO 3
<211> LENGTH: 9
<212> TYPE: PRT
<213> ORGANISM: Artificial Sequence
<220> FEATURE:
<223> OTHER INFORMATION: GHRsp (1-9)

<400> SEQUENCE: 3

Met Pro Ser Pro Gly Thr Val Cys Ser
1               5

<210> SEQ ID NO 4
<211> LENGTH: 10
<212> TYPE: PRT
<213> ORGANISM: Artificial Sequence
```

-continued

```
<220> FEATURE:
<223> OTHER INFORMATION: GHRsp (1-10)

<400> SEQUENCE: 4

Met Pro Ser Pro Gly Thr Val Cys Ser Leu
1               5                   10

<210> SEQ ID NO 5
<211> LENGTH: 23
<212> TYPE: PRT
<213> ORGANISM: Rattus norvegicus

<400> SEQUENCE: 5

Met Val Ser Ser Ala Thr Ile Cys Ser Leu Leu Leu Leu Ser Met Leu
1               5                   10                  15

Trp Met Asp Met Ala Met Ala
            20

<210> SEQ ID NO 6
<211> LENGTH: 23
<212> TYPE: PRT
<213> ORGANISM: Ovis aries

<400> SEQUENCE: 6

Met Pro Ala Pro Arg Thr Ile Tyr Ser Leu Leu Leu Leu Ser Leu Leu
1               5                   10                  15

Trp Met Asp Leu Ala Met Ala
            20

<210> SEQ ID NO 7
<211> LENGTH: 24
<212> TYPE: PRT
<213> ORGANISM: Sus scrofa

<400> SEQUENCE: 7

Met Pro Ser Thr Gly Thr Ile Cys Ser Leu Leu Leu Leu Ser Val Leu
1               5                   10                  15

Leu Met Ala Asp Leu Ala Met Ala
            20

<210> SEQ ID NO 8
<211> LENGTH: 23
<212> TYPE: PRT
<213> ORGANISM: Mus musculus

<400> SEQUENCE: 8

Met Leu Ser Ser Gly Thr Ile Cys Ser Leu Leu Leu Leu Ser Met Leu
1               5                   10                  15

Trp Met Asp Met Ala Met Ala
            20

<210> SEQ ID NO 9
<211> LENGTH: 23
<212> TYPE: PRT
<213> ORGANISM: Canis lupus

<400> SEQUENCE: 9

Met Pro Ser Leu Gly Thr Met Cys Ser Leu Leu Leu Phe Ser Val Leu
1               5                   10                  15

Trp Val Asp Leu Ala Met Ala
            20
```

```
<210> SEQ ID NO 10
<211> LENGTH: 23
<212> TYPE: PRT
<213> ORGANISM: Felis catus

<400> SEQUENCE: 10

Met Pro Ser Pro Gly Thr Val Cys Ser Leu Leu Leu Phe Ser Met Leu
1               5                   10                  15

Trp Ala Asp Leu Ala Met Ala
            20

<210> SEQ ID NO 11
<211> LENGTH: 24
<212> TYPE: PRT
<213> ORGANISM: Artificial Sequence
<220> FEATURE:
<223> OTHER INFORMATION: consensus sequence for GHRsp (1-23)

<400> SEQUENCE: 11

Met Pro Ser Pro Gly Thr Ile Cys Ser Leu Leu Leu Leu Ser Met Leu
1               5                   10                  15

Trp Met Ala Asp Leu Ala Met Ala
            20
```